(12) United States Patent
Czollner et al.

(10) Patent No.: US 6,369,238 B1
(45) Date of Patent: Apr. 9, 2002

(54) PROCESSES FOR THE PREPARATION OF DERIVATIVES OF 4A, 5, 9, 10, 11, 12-HEXAHYDRO-6H-BENZOFURO-[3A, 3, 2-EF][2]BENZAZEPINE

(75) Inventors: Laszlo Czollner, Neufeld; Johannes Fröhlich, Vienna; Ulrich Jordis, Vienna; Bernhard Küenburg, Vienna, all of (AT)

(73) Assignee: Sanochemia Pharmazeutica, Boltzmanngasse (AT)

( * ) Notice: Subject to any disclaimer, the term of this patent is extended or adjusted under 35 U.S.C. 154(b) by 0 days.

(21) Appl. No.: 09/814,778

(22) Filed: Mar. 23, 2001

Related U.S. Application Data

(60) Division of application No. 09/296,609, filed on Apr. 23, 1999, which is a division of application No. 08/839,350, filed on Apr. 18, 1997, now Pat. No. 6,043,359, which is a continuation-in-part of application No. 08/487,102, filed on Jun. 7, 1995, now abandoned.

(30) Foreign Application Priority Data

Oct. 21, 1994 (AT) ............................................... 1980/94
Oct. 23, 1995 (WO) ............................... PCT/AT95/00208

(51) Int. Cl.⁷ .......................................... C07D 209/56
(52) U.S. Cl. ..................................................... 548/421
(58) Field of Search ........................................ 548/421

(56) References Cited

U.S. PATENT DOCUMENTS

| | | | |
|---|---|---|---|
| 4,290,862 A | 9/1981 | Vlahov et al. | 205/424 |
| 4,663,318 A | 5/1987 | Davis | 514/215 |
| 5,428,159 A | 6/1995 | Shieh et al. | 540/581 |

FOREIGN PATENT DOCUMENTS

| | | |
|---|---|---|
| DE | 29 45 161 | 6/1980 |
| WO | WO 88/08708 | 11/1988 |

OTHER PUBLICATIONS

Barton et al., "The Synthesis of Galanthamine", Proc. Chem. Soc., 392–393 (1960).
Barton et al., "Phenol Oxidation and Biosynthesis Part. V. The Synthesis of Galanthamine", J. Chem. Soc. 806–817 (1962).
Kametani et al., "Studies on the Syntheses of Heterocyclic Compounds Part CCCXV. Modified Total Synthesis of (±)-Galanthamine Through Phenol Oxidation", J. Chem. Soc., 2602–2605 (1969).
Kametani et al., "Modified Total Synthesis of (±) Galannthamine Through Phenol Oxidation", J. Chem. Soc. Chem. Comm., 425–426 (1969).
Kametani et al., "Studies on the Syntheses of Heterocyclic Compounds, Part CCCLXXXVI, Alternative Total Syntheses of Galanthamine and N–Benzylgalanthamine Iodide", J. Chem. Soc., 1043–1047 (1971).

Kametani et al., "Studies on the Syntheseis of Heterocyclie Compounds, Part DVII(1), A Synthesis of (±)–N–Norgalanthamine", J. Het. Chem., 10:35–37 (1973).
Kametani et al., "Studies on the Synthesis of Heterocyclic Compounds, CCCXCVI, An Alternative Total Synthesis of (±)–Galanthamine," J. Org. Chem., 36:1295–97 (1971).
Szewczyk et al., "An Improved Synthesis of Galanthamine", J. Het. Chem., 25:1809–1811 (1988).
Vlahov et al., "Synthese Von Biologisch Aktiven Naturstoffen", Izv. Khim., 20:59–71 (1987).
Krikorian et al., "Synthesis of Galanthamine: Intramolecular Para–Ortho–Coupling of Diaryl Ethers by Anodic Oxidation", Tetrahedron Lett., 25:2969–2972 (1984).
Vlahov et al., "Synthesis of Galanthamine and Related Alkaloids—New Approaches", Tetrahedron, 45:3329–3345 (1989).
Shimizu et al., "A Biogenetic–type Asymmetric Synthesis of Optically Active Amarylllidaceae Alkaloids: (+)–and (−)–Galanthamine from L–Tyrosine", Heterocycles, 8:277–282 (1977).
Yardley et al., "Introduction of the Methoxymethyl Ether Protecting Group", Synth., 244 (1976).
Kametani et al., "The Optical Resolution of (±)–Galanthamine", Heterocycles, 4:1111–14 (1976).
Anonymous, Synform, 183–94 (1983); Chemical Abstracts, 100(15):121402z.
Kametani et al., "Studies on the Syntheses of Heterocyclic Compounds, Part CCCXV, Modified Total Synthesis of (±)–Galanthamine Through Phenol Oxidation", J. Chem. Soc., 2602–05 (1969).
Holton et al., "Palladium–Mediated Biomimetic Synthesis of Narwedine", Am. Chem. Soc., 110:314–316 (1988).
Shieh et al., "Asymmetric Transformation of Ether Enantiomer of Narwedine via total Spontaneous Resolution Process, A Concise Solution to the Synthesis of (−)–Galanthamine", J. Org. Chem., 59:5463–5465 (1994).

(List continued on next page.)

*Primary Examiner*—Bruck Kifle
(74) *Attorney, Agent, or Firm*—Morgan, Lewis & Bockius LLP

(57) ABSTRACT

The invention relates to processes for the preparation of 4a,5,9,10,11,12-hexahydro-6H-benzofuro[3a,3,2-ef][2] benzazepine, or derivatives thereof. Furthermore, the invention also relates to the compounds formed during the preparation of 4a, 5,9,10,11,12-hexahydro-6H-benzofuro[3a,3,2-ef][2]benzazepine.

2 Claims, No Drawings

OTHER PUBLICATIONS

Smith et al., "2–Hydroxymethyl–2–Cyclopenteone", Organic synthesis Coll. vol., 7:271–275 (1988).

Hagedorn et al., "Bicyclo[3.3.0]octane–2,6–dioneand Bicyclo[3.3.0]octa–3,7–dione–2,6–dione", J. Org. Chem., 42:3765–67 (1977).

Shimizu et al., "Sterochemical Studies, LIV, A Biogenetic–type Asymmetric Synthesis of Optically Active Galanthamine from L–Tyrosine", Chem. Pharm. Bull., 26:3765–71 (1978).

Baraka et al., "Reversal of Central Anticholinergic Syndrome by Galanthamine", JAMA, 238:2293–2294 (1977).

Corey, E.J., et al., J. Am. Chem. Soc., vol. 115:9327–9328 (1993).

Carey, F.A., et al., "Advanced Organic Chemistry", Plenum Press, NY, Part B, 232–244 (1990).

March, J., "Advanced Organic Chemistry", Wiley & Sons, NY, 566–567 (1992).

Edwards, R.L., et al., Constituents of the Higher Fungi. Part II. The Synthesis of Hispidin., J. Chem. Soc. 5003 (1961).

Saraf, S.D., "Relation of Thionyl Bromide with Aromatic Aldehydes", Synth. Commun., 13:7 (1983).

PROCESSES FOR THE PREPARATION OF DERIVATIVES OF 4A, 5, 9, 10, 11, 12-HEXAHYDRO-6H-BENZOFURO-[3A, 3, 2-EF] [2]BENZAZEPINE

This is a divisional of co-pending application Ser. No. 09/296,609, filed on Apr. 23, 1999, which is a divisional of co-pending application Ser. No. 08/839,350, filed on Apr. 18, 1997, now U. S. Pat. No. 6,043,359, which is a continuation-in-part of patent application Ser. No. 08/487,102, filed on Jun. 7,1995, now abandoned.

The invention relates to processes for the preparation of derivatives of 4a, 5,9,10,11,12-hexahydro-6H-benzofuro [3a,3,2-ef] [2]benzazepine, of the general formula (I)

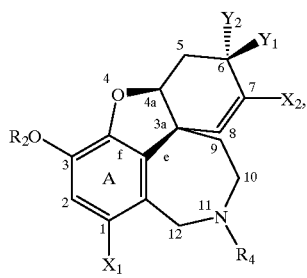

(I)

or of salts thereof, wherein $R_2$, $R_4$, $X_1$, $X_2$, $Y_1$ and $Y_2$ are either identical or different and are hydrogen, fluorine, chlorine, bromine, iodine, a hydroxyl or alkoxy group, a lower, optionally branched alkyl group which is optionally substituted by, for example, at least one halogen, a lower, optionally branched alkenyl, group, a lower, optionally branched alkynyl group, an optionally substituted aryl, aralkyl or aryloxyalkyl group, the alkyl chain of which is optionally branched and the aromatic nucleus of which is optionally substituted, formyl or unbranched or branched alkylcarbonyl, arylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens, or $Y_1$ and $Y_2$ together are =O and wherein A is a benzene nucleus which is optionally mono- or polysubstituted by at least one lower, optionally branched alkyl group, at least one lower, optionally branched alkene group, at least one lower, optionally branched alkyne group, at least one lower, optionally branched alkoxy group, by fluorine, chlorine, bromine or iodine or by several identical or different halogens, at least one alkyl group substituted by one halogen or by several identical or different halogens, such as chloromethyl and trifluoromethyl, at least one optionally substituted aralkyl group and/or at least one hydroxyl group, primary, secondary or tertiary amino group, nitro group, nitrile group, alkylamino group, arylamino group, aldehyde group, carboxylic acid group or all derivatives of the carboxylic acid group, such as eaters, asides and halides.

The invention furthermore relates to processes for the preparation of derivatives of 4a,3,9,10,11,12-hexahydro-6H-benzofuro[3a,3,2-ef] [2]benzazepine, of the general formula (II)

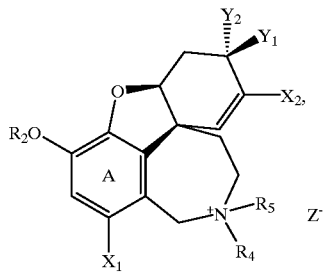

(II)

wherein $R_2$, $R_4$, $X_1$, $X_2$, $Y_1$, and $Y_2$ and A have the meanings given above for formula (I), $Z^-$ is an organic anion of a pharmaceutically useful acid, such as tartrate, lactate, citrate, acetate or maleate, or an inorganic anion, such as fluoride, chloride, bromide, iodide, sulfate, phosphate or chlorate, $R_5$ is hydrogen, formyl, unbranched or branched alkyl, alkenyl, aryl, aralkyl, alkylcarbonyl, arylcarbonyl or aralkylcarbonyl which are unsubstituted or substituted by at least one halogen, or branched or branched alkyloxycarbonyl aryloxycarbonyl, aralkyloxycarbonyl, alkylsulfonyl, aryl-sulfonyl or aralkylsulfonyl which are unsubstituted or substituted by one or more halogens.

Preferred meanings of the substituents $R_1$–$R_6$, $X_{1,2}$ $Y_{1,2}$ are $R_1$, $R_2$, $R_3$, $R_6$: hydrogen, unbranched or branched alkyl, alkenyl, aryl, aralkyl, alkylcarbonyl, arylcarbonyl or aralkylcarbonyl which are unsubstituted or substituted by one or more halogens, or any combination of these radicals, $X_1$, $X_2$: H, F, Cl, Br, I⁻, t-butyl and any combination, $Y_1$, $Y_2$: H, O–$R_6$, and $Y_1$ and $Y_2$=0, $R_4$, $R_5$: the preferred meanings mentioned for $R_1$, $R_2$, $R_3$, $R_6$ and unbranched or branched alkyloxycarbonyl, aryloxycarbonyl aralkyloxycarbonyl, alkylsulfonyl, arylsulfonyl or aralkylsulfonyl which are unsubstituted or substituted by one or more halogens.

Galanthamine is an alkaloid of high pharmacological activity which occurs chiefly in plants of the Amaryllidaceae type. Its action as a selective acetylcholinesterase inhibitor and its associated use for Alzheimer's diseases are to be emphasized in particular. Galanthamine has been isolated to date from the caucasian snowdrop Galanthus woronoyi in amounts of a few kg annually at a cost of more than US$ 30,000/kg. Galanthamine syntheses have been known in principle since the end of the nineteen-sixties, but long, uneconomical reaction paths with poor overall yields have been used.

The synthesis of some compounds of the general formulae (I) and (II) given above is known per se and described in the literature. Thus N-(3-hydroxy-4-methoxyphenyl)-N-methyl-4-hydroxy-phenylethylamine has been subjected to oxidative cyclization with the aid of various oxidizing agents to give narwedine derivatives (narwedine is the precursor to galanthamine, but already has the ring structure characteristic of galanthamine) [Lit. 1–2], the yields as a rule being less than 1% of theory. Although the structure could thus be demonstrated galanthamine could not be prepared in kg amounts of pharmaceutical interest.

Optimized processes (above all Kametani, Lit. 3–7,22) describe this cyclization an N-methyl-benzamide and phenylacetamide derivatives in yields of up to 40%, but the poor overall yields render industrial utilization impossible. The literature furthermore reports the cyclization of N,N-disubstituted phenylethylamine derivatives (Lit. 8) and electrochemical (Lit. 9–12), microbiological, enzymatic (Lit. 8) and biomimetic methods (Lit. 14–15). Lit. 23 describes the preparation of narwedine from isovanillin in an overall yield of 44%, but the use of equimolar amounts of palladium and also thallium trifluoroacetate render this synthesis uneconomical. (+/−) Narwedine obtained by this route (Lit. 23) is enriched in the desired (−) narwedine in Lit. 24 and converted into galanthamine with L-Selektride in a good yield.

Lit. 8 proposes a synthesis in which the oxidative cyclization is described with a yield of 21%, but separation of the enantiomers is absent. The reduction of bromonarwedine with $LiAlH_4$ in THF to form a 53:31 diastereomer mixture of (+/−) galanthamine and (+/−) epigalanthamine is also known.

The invention is based an the object of developing a synthesis process with which larger amounts of the title substances can be prepared in a reproducible manner and in improved yields both of the individual steps and of the overall yield.

This object is achieved according to the invention by the processes according to claim 1 and 2, the sub-claims relating to preferred and advantageous variants and embodiments of the invention. In particular, the following measures of the invention have proved to be advantageous:

Replacement of halogenated solvents, for example chloroform, by toluene. Halogenated solvents are nowadays scarcely still employed as industrial solvents because of their toxicity, the difficulties of their disposal and their ecological unacceptability. Toluene, in contrast, does not have these disadvantages.

Working up by extraction requires organic solvents. With the invention, the working up operations of most stages can be optimized such that the reaction product can usually be obtained in crystalline form from the solution. Chromatographic purification stages or extractions can thus mostly be avoided.

Furthermore, the yields can be reproduced within a very narrow range in the invention by improving the parameters and the purity of the main products and the content of by-products can be defined according to these reactions. Improved and reproducible yields of the individual stages and of, the overall yield are possible with the process of the invention. The invention provides, inter alia, a process in which bromoformylnarwedine is reduced with reducing agents. L-Selektride can be used as the reducing agent, the reduction leading diastereoselectively to N-demethylbromogalanthamine in a high yield (for example 85%), which can be converted into (±) galanthamine by N-methylation according to Eschweiler-Clark and debromination. In this process, it has not been possible to detect (+/−) epigalanthamine in the reaction product by chromatographic methods. Galanthamine and galanthamine derivatives can be prepared on an industrial scale by the process according to the invention via intermediates which are not described in the literature (see the compounds mentioned in claims 64 to 67).

The processes of the present invention, which are considerably improved with respect to yield and purity of the resulting products compared with the prior art and can be carried out on an industrial scale, can be described by way of example as follows:

For synthesis of derivatives of 4a,5,9,10,11,12-hexahydro-6H-benzofuro[3a,3,2-ef] [2]benzazepine, of the general formula (I)

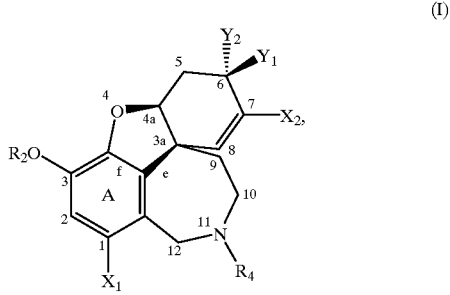

(I)

or of salts thereof, wherein $R_2$, $R_4$, $X_1$, $X_2$, $Y_1$ and $Y_2$ are either identical or different and are hydrogen, fluorine, chlorine, bromine, iodine, a hydroxyl or alkoxy group, a lower, optionally branched and optionally substituted alkyl group, a lower, optionally branched alkene group, a lower, optionally branched alkyne group, an optionally substituted aryl, aralkyl or aryloxyalkyl group, the alkyl chain of which is optionally branched and the aromatic nucleus of which is optionally substituted, a formyl group, at unbranched or branched alkylcarbonyl, arylcarbonyl, aralkyl carbonyl, alkyloxycarbonyl, aryloxycarbonyl, aralkyloxycarbonyl, alkylsulfonyl, aralkylsulfonyl or arylsulfonyl which are unsubstituted or substituted by one or more halogens and $Y_1$, $Y_2$ can be =O (ketone), wherein A is a benzene nucleus, which is optionally mono- or polysubstituted by at least one lower, optionally branched alkyl, group, at least one lower, optionally branched alkene group, at least one lower, optionally branched alkyne group, at least One lower, optionally branched alkoxy group, by fluorine, chlorine, bromine or iodine or by several identical or different halogens, at least monosubstituted alkyl group [sic], such as chloromethyl and trifluoromethyl, at least one optionally substituted aralkyl group, at least one hydroxyl group, primary, secondary or tertiary amino group, nitro group, nitrile group, alkylamino group or arylamino group, aldehyde group, carboxylic acid group and all derivatives of the carboxylic acid group, such as esters, amides and halides, a process is used comprising a condensation step with subsequent reduction, an N-formylation or introduction of an N-protective group, a bromination (which can also already be carried out at the stage of isovanillin in accordance with the overall equation), in oxidative cyclization, a reduction, depending on the mature of the reducing agent also additionally an N-methylation and debromination, and a separation of the optical isomers. If required, individual process steps of those mentioned can also be omitted.

The present invention also relates to the preparation of salts of the title compounds.

The compounds of the general formula (I) can be converted into salts with organic and inorganic acids, for example:

of mineral acids, such as hydrochloric and hydrobromic acid, sulfuric acid and phosphoric acid, and perchloric acid, or pharmaceutically acceptable Organic acids, such as lactic acid, substituted and unsubstituted tartaric acid, acetic acid, salicylic acid, citric acid, benzoic acid, β-naphthoic acid, adipic acid and the like.

The processes of the invention in some cases lead to new compounds. The new compounds include:

bromogalanthamine of the formula

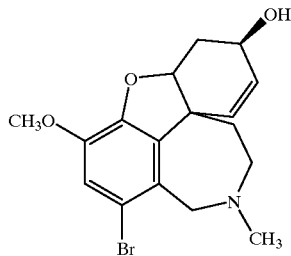
(1)

epibromogalanthamine of the formula

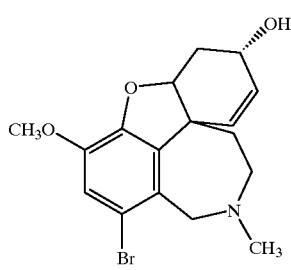
(2)

N-demethylbromogalanthamine of the formula

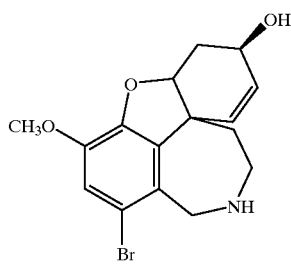
(3)

and

N-demethyl-epibromogalanthamine of the formula

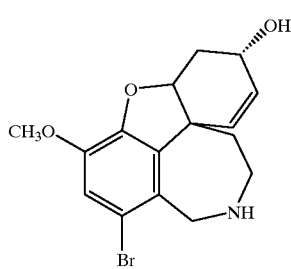
(4)

The invention also relates to the preparation of salts of the substituted derivatives of 4a,5,9,10,11,12-hexahydro-6H-benzofuro[3a,3,2-ef]benzazepine, of the general formula (II)

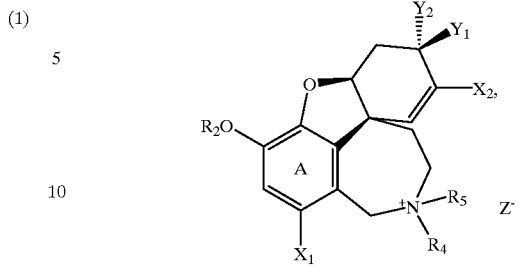
(II)

in which $R_2$, $R_4$, $X_1$, $X_2$, $Y_1$ and $Y_2$ and A have the meanings given above for formula (I) and $Z^-$ is an organic anion of a pharmaceutically useful acid, such as tartrate, lactate, citrate, acetate, maleate and the like, or an inorganic anion, such an a fluorine, chlorine, bromine or iodine anion, or a sulfate or phosphonate or chlorate anion, $R_5$ is a hydrogen atom, a lower, unbranched or branched alkyl radical, aryl or an aralkyl radical which is branched or unbranched in the alkyl chain, by the process described above by way of example.

The compounds obtainable according to the invention and salts thereof contain at least two asymmetric cantors and therefore occur in several stereoisomeric forms. The invention also relates to the separation of the resulting diastereomers or racemates into the optically puts antipodes and mixtures thereof.

The abovementioned steps can be carried out generally and by way of example an follows:

1. Condensation and reduction

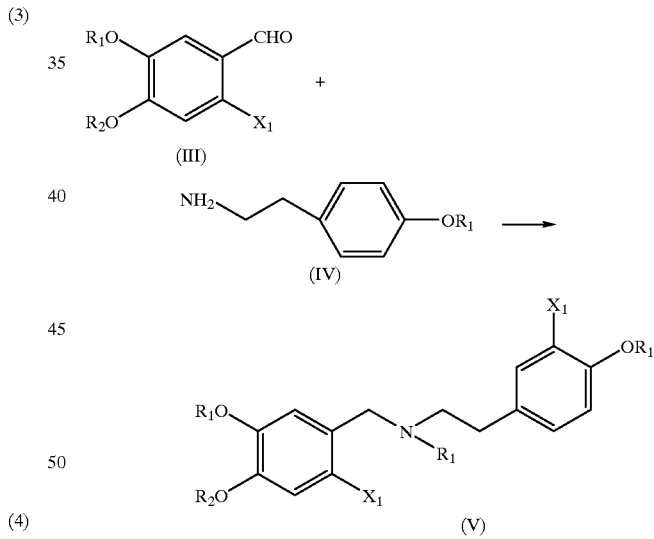

To prepare the compounds of the general formulae (I) and (II), substituted derivatives of the general formula (V) where $R_4$=H are prepared by a procedure in which a compound of the general formula (III) wherein $R_1$ and $R_2$ are hydrogen, a lower, unbranched or branched alkyl or an aryl or aralkyl which is branched or unbranched in the alkyl chain, as well as alkyl-carbonyl, aryl-carbonyl and aralkylcarbonyl, or together ($R_1$=$R_2$=—$CH_2$—) an alkyl group or a combination of these radicals, $X_1$=H, fluorine, chlorine, bromine, iodine or t-butyl is subjected to a condensation reaction with tyramine or substituted tyramine ($R_3$=hydrogen, a lower unbranched or branched alkyl, aryl or an aralkyl which is branched or unbranched in the alkyl chain, as well as alkylcarbonyl, arylcarbonyl, and aralkylcarbonyl). The procedure here can be as follows:

An equimolar solution of (III) and (IV) in toluene, xylene or benzene or mixtures of these solvents with higher alcohols, chiefly toluene with n-butanol, in ratios of 9:1 to 1:9, chiefly 1:1, in concentrations of 1–30%, is reacted at the reflux temperature and water is separated off. The solvent is then separated off by distillation and recovered to the extent of >95%, and the is dissolved in alcohol, such as methanol, ethanol, n-propanol, i-propanol, methylglycol or ethylglycol, water, glacial acetic acid or mixtures of these solvents, chiefly methanol, in concentrations of 1–30% and reduced by addition in portions of 0.6 to 5 equivalents, preferably 0.65 to 0.7 equivalent, of reducing agents, such as sodium borohydride, potassium borohydride, sodium cyanoborohydride and $LiAlH_4$, and mixtures of these, but chiefly sodium borohydride, in powder or granule form, at a temperature from –30° C. up to the reflux temperature. The condensation product (V) is filtered off from the alcoholic solution as the first fraction by filtration in yields of 80 to 85%. Working up of the alcoholic solution by distillation to 15 to 30% of the volume and filtration of the 2nd fraction increases the yield to 90 to 95% of theory. Alternatively, the reaction solution can be poured onto water, whereupon crystalline product (V) precipitates out and, after filtration with suction and drying, is obtained in yields of up to 95%.

2. N-Formylation or N-protective group:

Starting compounds for the oxidative cyclization of the formula (V) where $R_4$=formyl or unbranched or branched aralkyl, alkylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens are prepared by reaction of the compounds (V) where $R_4$=H with the corresponding acids, esters, anhydrides, halides, azides, carbonates or other reactive derivatives of these protective groups.

In particular, a compound of the general formula (V) where $R_4$=H can be reacted in solvents such as THF, dioxane, DMF, toluene, xylene or mixtures of these solvents with the equimolar to 50 times the molar amount of the ethyl formate and catalytic amounts of formic acid (0.001 to 1 equivalent) at a temperature from 0° C. to the reflux temperature to give a compound of the general formula (V) where $R_4$=CHO. The solvents are removed in this process by vacuum distillation, the distillation residue crystallizes by addition in portions of water and ice and the product is obtained in yields of >90% at a content of >95% by filtration.

3. Bromination:

If, in compounds of the general formula (V) where $R_1$, $R_2$, $R_3$=a lower unbranched or branched alkyl, aryl, aralkyl, alkylcarbonyl, arylcarbonyl or aralkylcarbonyl, $X_1$, $X_2$=H, $R_4$=formyl, or unbranched or branched aralkyl, alkylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens, with a content of 90 to 100% in solvent mixtures of halogenated hydrocarbons, such as chloroform or methylene chloride, with alcohols (methanol, ethanol, methylglycol, ethylglycol, ethylene glycol, n-propanol, i-propanol) in ratios of 9:1 to 1:9, preferably 3:2 to 2:3, and of pure alcohols (methanol, ethanol, methylglycol, ethylglycol, ethylene glycol, n-propanol, i-propanol) and mixtures thereof with one another, preferably ethanol/methylglycol, in ratios of 9:1 to 1:9, preferably 3:2 to 2:3, with water contents of 0 to 5%, preferably 0 to 0.2%, at a temperature of –80 to +60° C., preferably –40 to 0° C., in a concentration of 0.5 g to 20 g/100 ml of solvent, the reaction is carried out with 1.0 to 3.0, preferably 1.4 to 1.7 equivalents of a bromine reagent which is obtained by addition of elemental bromine into the solvents mentioned in a concentration of 1 to 90%, preferably 2 to 10%, with addition times of the bromine reagent of 10 minutes to 4 hours, preferably 15 to 30 minutes, the compound of the formula (V) where $X_1$=Br is obtained in yields of 90 to 96% of theory after a reaction time of 0.5 to 24 hours, preferably 30 to 60 minutes, and after working up (concentration by distillation to 10 to 25% of the volume and pouring onto 10 to 50 times the amount of ice-water, filtration and drying).

Preparation of the intermediate (V) where $X_1$=Br, $R_4$=CHO or polybrominated intermediate:

Route 1 (see page 24, overall equation): if a compound of the formula (V) where $X_1$, $X_2$=H and $R_4$=CHO is brominated in accordance with the working instructions given, for example, 82% of product, 6% of precursor, 8% of by-product where $X_2$=Br and 5% of more highly brominated products are obtained. (HPLC, Lichrosorb RP 18, 5μ, 300/4 mm, eluant $MeOH/H_2O$ 6:4 at 280 nm). If the bromination method is changed, the ratios of the products stated also change (a higher content of more highly brominated products is usually formed). After the oxidative cyclization, in addition to the desired compound of the general formula (I) where $X_1$=Br, $R_4$=CHO and $Y_1$=$Y_2$=O, [lacuna] could be detected in the precursor in contents corresponding to the content of the compound of the general formula (V) where $X_1$=$X_2$=Br, $R_4$=CHO (HPLC, Lichrosorb Si 60, 10μ, 300/4 mm, eluant: $CHCl_3$/MeOH 95:5 at 254 nm) and isolated by means of preparative chromatography (silica gel 60, $CHCl_3$:MeOH 1–5%). After reduction with L-Selektride or with other reducing agents, more highly brominated narwedine ($X_1$=$X_2$=Br) is either likewise reduced to galanthamine or separated off by preparative chromatography.

Route 2: (see page 24, overall equation). Starting from veratrumaldehyde, via 6-bromo-isovanillin, the compound of the formula (V) where $X_1$=Br, $R_4$=CHO can be prepared by condensation and N-formylation without more highly brominated by-products.

4. Oxidative cyclization:

For oxidative cyclization of compounds of the general formula (V) where $R_2$=hydrogen, a lower, branched or unbranched alkyl, aryl, or an aralkyl which is branched or unbranched in the alkyl chain, or alkyl-carbonyl, arylcarbonyl and aralkyl-carbonyl or a combination of these radicals $X_1$=H, fluorine, chlorine, bromine, iodine or t-butyl, $R_4$=formyl, or unbranched or branched aralkyl, alkylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens, $R_3$=hydrogen, to give a compound of the general formula (I) where $R_2$, $R_4$, $X_1$ are as above, $Y_1$, $Y_2$=O (ketone) and $X_2$=H or Br, the reaction is carried out in solvents, such as chloroform, methylene chloride, ethyl acetate, THF, dioxane, glacial acetic acid, water, mixtures thereof with alcohols (methanol, ethanol, methylglycol, ethylglycol, ethylene glycol, n-propanol, i-propanol) in ratios of 9:1 to 1:9, and also toluene, xylene or benzene, chiefly xylene and toluene, in a concentration of 0.05 g to 10 g/100 ml of solvent, with bases, such as sodium hydrogencarbonate, potassium carbonate, NaOH, KOH or pyridine, preferably potassium carbonate, in a concentration of 0.1% to a saturated solution or suspension, chiefly 5 to 20%, and oxidizing agents, such as Pb(OAc)$_4$, KMnO$_4$, FeCl$_3$, potassium ferricyanide of H$_2$O$_2$, preferably potassium ferricyanide, 4–10 equivalents, preferably 5.5–6 equivalents, if necessary with addition of phase transfer catalysts, such as Aliquat or crown ethers, as well as ascorbic acid, CuCl or trifluoroacetic acid, at a temperature from −40° C. to the reflux temperature, chiefly 50 to 80° C., and by rapid addition or addition in portions of the precursor as a solid, as a solution or as a suspension in a solvent, preferably as a solid, with a reaction time of 10 minutes to 72 hours, chiefly 15 to 45 minutes, with vigorous mechanical stirring, preferably using a stirrer and a homogenizer, if necessary under an inert gas, such as N$_2$, CO$_2$ or argon, chiefly argon. Working up by filtration, phase separation and vacuum distillation of the toluene phase gives the crude product in yields of 5 to 65%, from which yields of 5 to 50% are obtained by purification of the cyclization products.

5. Reduction:

For reduction of compounds of the general formula (I) in which R$_2$ is a lower unbranched or branched alkyl, aryl, aralkyl, alkylcarbonyl, arylcarbonyl or aralkylcarbonyl, X$_1$, X$_2$ are fluorine, chlorine, bromine, iodine or t-butyl, R$_4$ is formyl, or unbranched or branched aralkyl, alkylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens and Y$_1$, Y$_2$=O (bromonarwedine type), with hydride reagents, such as DiBAl—H, DiBAl—H/ZnCl$_2$, Al isopropylate, Red-Al, K-Selektride, L-Selektride, KS-Selektride, LS-Selektride, Li-tri-t-butoxy-AlH, Li-tri-ethoxy-AlH, 9-BBN, Superhydride, NaBH$_4$, Zn(BH$_4$)$_2$, AlH$_3$, AlCl$_2$H or a combination of these reducing agents, a procedure can be followed in which the reduction is carried out by addition of the reducing agent in equimolar amounts or in excess to the starting substance or inverse addition of the starting substance to the reducing agent in an inert solvent, such as diethyl ether, THF, dioxane, toluene, xylene or benzene, at temperatures from −50° C. to the reflux temperature. After alkaline (chiefly NH$_4$OH) or acid (chiefly 2N HCl) working up and subsequent extraction with solvents such as toluene, xylene, benzene, ethyl acetate, ether, chloroform or methylene chloride, the crude product is purified by chromatographic processes and, as required, the diastereomers are isolated or the crude products are reacted further directly.

In particular, N-demethylbromogalanthamine is obtained diastereoselectively in yields of 70–85% of theory, after purification by column chromatography, by reduction of bromo-N-formylnarwedine (in contrast to Lit. 24, where narwedine is used) with L-Selektride or K-Selektride. No epi-N-demethylbromogalanthamine could be detected by chromatographic methods.

N-demethylbromogalanthamine is converted into bromogalanthamine in yields of 80–90% of theory by N-methylation, for example by boiling up for 10 minutes to several hours in a 5- to 50-fold excess of formic acid and aqueous formaldehyde solution.

Bromogalanthamine is converted into galanthamine, for example, by heating at the reflux temperature with a 5- to 50-fold molar excess of formic acid and triethylamine in the presence of 0.1 to 15% of palladium/active charcoal catalyst for 1 to 12 hours, bromine being eliminated. Yield: 70 to 80% of theory.

The reaction stages can also be carried out without isolation and purification of the intermediates.

A mixture of N-demethylbromogalanthamine and epi-N-demethylbromogalanthamine in a ratio of about 1:1 is obtained by reduction of the precursor with Li-tri-t-butoxy-AlH.

Reduction with DiBAl—H gives 43% of bromogalanthamine and 41% of epibromogalanthamine.

Reduction with Li—AlH$_4$/anhydrous H$_2$SO$_4$ also gives bromogalanthamine and epibromogalanthamine in a ratio of about 3:1.

The reduction can be carried out, for example, as described below:

For reduction of a compound of the general formula (I) with R$_2$=alkyl, X$_1$=Br, R$_4$=CHO, X$_2$=H, Y$_1$, Y$_2$=O (ketone), the precursor is dissolved in a solvent such as THF, dioxane or other ethers, chiefly THF, in concentrations of 0.1 to 20 g/100 ml by heating. 3 to 5, chiefly 3.5 equivalents of L-Selektride, chiefly as a 1 molar solution in THF, are then added at a temperature of from −50° C. to the reflux temperature, chiefly at 0–20° C., and the mixture is reacted by stirring for 20 minutes to 48 hours, chiefly one hour. The complex formed with the reducing agent is destroyed by addition of water and ammonium hydroxide and excess organic solvent is evaporated off in vacuum by heating to not more than 30° C. Extraction with solvents such as ethers (e.g. diethyl ether), ethyl acetate, butyl acetate, chloroform, methylene chloride, toluene, benzene or xylene gives N-demethylbromogalanthamine in crude yields of 90 to 100% of theory.

For monomethylation of N-demethylbromogalanthamine, a solution of N-demethylbromogalanthamine in a 5- to 30-fold molar excess of formic acid and aqueous formaldehyde solution (37%) is heated at the reflux temperature, with or without an organic solvent, for 10 minutes to 2 hours, chiefly 15 to 20 minutes.

For debromination of bromogalanthamine or epibromogalanthamine, bromo- or epibromogalanthamine is heated at the reflux temperature in a 5- to 50-fold molar excess of formic acid and triethylamine, with or without an organic solvent, in the presence of 0.1 to 15% of palladium/active charcoal catalyst for 1 to 12 hours, chiefly 2.5 hours.

For reduction of a compound of the general formula (I) where R$_2$=alkyl, X$_1$=Br, R$_4$=CHO, X$_2$=H, Y$_1$, Y$_2$=O (ketone), the precursor is suspended in an inert organic solvent, such as benzene, toluene or xylene, chiefly toluene, in a concentration of 0.1 to 20 g/100 ml, and 3 to 5, chiefly 3.5 equivalents, of DiBAl—H, as a chiefly 1.5 molar solution in toluene, are added dropwise at a temperature from −50° C. to reflux temperature, chiefly 0 to 20° C. The mixture is then stirred at this temperature for 20 minutes to 12 hours, chiefly 30 minutes to 1.5 hours, the complex formed is destroyed with water and ammonium hydroxide, the mixture is extracted with toluene and the crude product (90 to 100% of theory) is separated into 43% of bromogalanthamine and 41% of epibromogalanthamine by means of column chromatography (silica gel, acetone/hexane 1:1).

6. Separation of optical isomers:

To separate chiral 4a,5,9,10,11,12-hexahydro-6H-benzofuro[3a,3,2-ef] [2] benzazepines of the general formula (I), (Y$_1$=H, OH; Y$_2$=, OH) in which A, R$_2$, R$_4$, X$_1$ and X$_2$ have the abovementioned meanings, into the enantiomerically pure antipodes, the method of fractional crystallization of salts with chiral acids can be used. The separation of the (+) and (−) isomers of the compounds of the narwedine type (compounds of the general formula (I) in which Y$_1$ and Y$_2$ together are =O (ketone)) by fractional crystallization is carried out by a procedure in which a solution or suspension of the optical isomer mixture in 5 to 50 times the amount of a solvent, such as water, methanol, ethanol, propanol, isopropanol, acetone or mixtures of these solvents, chiefly methanol, is combined with the equimolar amount or an excess of a chiral acid (unsubstituted or monoor polysubstituted + or − tartaric acid, citric acid, lactic acid, α-methoxyphenylacetic acid, camphorsulfonic acid and derivatives thereof, preferably di-p-tolyl (+) tartaric acid), which is dissolved in one of the abovementioned solvents, the solution is seeded with crystals prepared from naturally occurring (−) galanthamine derivatives and chiral organic acids, such as di-p-tolyl (+) tartaric acid, and left to stand at −40 to +20° C., preferably 0° C., for 2 to 24 hours or longer, and the crystals formed are filtered off and dried, excess $NH_4OH$ is then added, the mixture is extracted with organic solvents, such as chloroform, methylene chloride, ethyl acetate, butyl acetate, diethyl ether, t-butyl methyl ether, dibutyl ether, petroleum ether, xylene, benzene, toluene or similar solvents, and the corresponding (−) galanthamine derivative is isolated by distillation of the solvent.

In this process, concentration of the mother liquor, taking up in excess $NH_4OH$, extraction with an organic solvent (as mentioned above) and evaporation gives further fractions of galanthamine, from which the (+) galanthamine derivatives can be obtained in a manner analogous to that above with the aid of the chiral organic acids, such as, for example, di-p-tolyl (−) tartaric acid.

The products obtained according to the invention can be purified by a process customary in chemistry, for example fractional distillation, crystallization or chromatography.

W. C. Shieh and J. A. Carlson report in J. Org. Chem. 1994, 59, 5463–5465 the (−)galanthamine is a selective acetylcholinesterase inhibitor which strengthens the cholinergic function and is considered as a product for treating individuals suffering from Alzheimer's disease.

In order to prepare enantiomerically pure (−)galanthamine it is proposed to add catalytic amounts of (−)narwedine seed crystals or (+)-galanthamine seed crystals to (±)narwedine in solution and to allow crystallization to take place. In this procedure, (−)narwedine crystallizes out in the form of white crystals from the solution containing (±)narwedine. To convert (−)narwedine to (−)galanthamine by reduction, a diastereoselective reduction of enantiomerically pure narwedine is proposed. (−)Narwedine obtained by the diastereoselective crystallization is reduced stereospecifically by means of L-Selektride to (−)galanthamine in a yield of almost 99% at −78° C. For the two-stage process (crystallization and reduction), overall yields in the conversion of racemic narwedine to (−)galanthamine of 90% are quoted. With regard to the preparation of (±)narwedine reference is made to Lit. 23 (Holton et al.), a method in which stoichiometric amounts of palladium and thallium are required.

One of the disadvantages of the process described is that the reduction has to be carried out under the described process conditions at −78° C. Furthermore, only a semi-microbatch (285 mg of precursor) is described, which is carried out in about 200 times the amount of solvent and is worked up chromatographically using $CH_2Cl_2$/methanol (6:1).

Reaction equations of the processes according to the invention are shown below.

Overall Reaction Equation

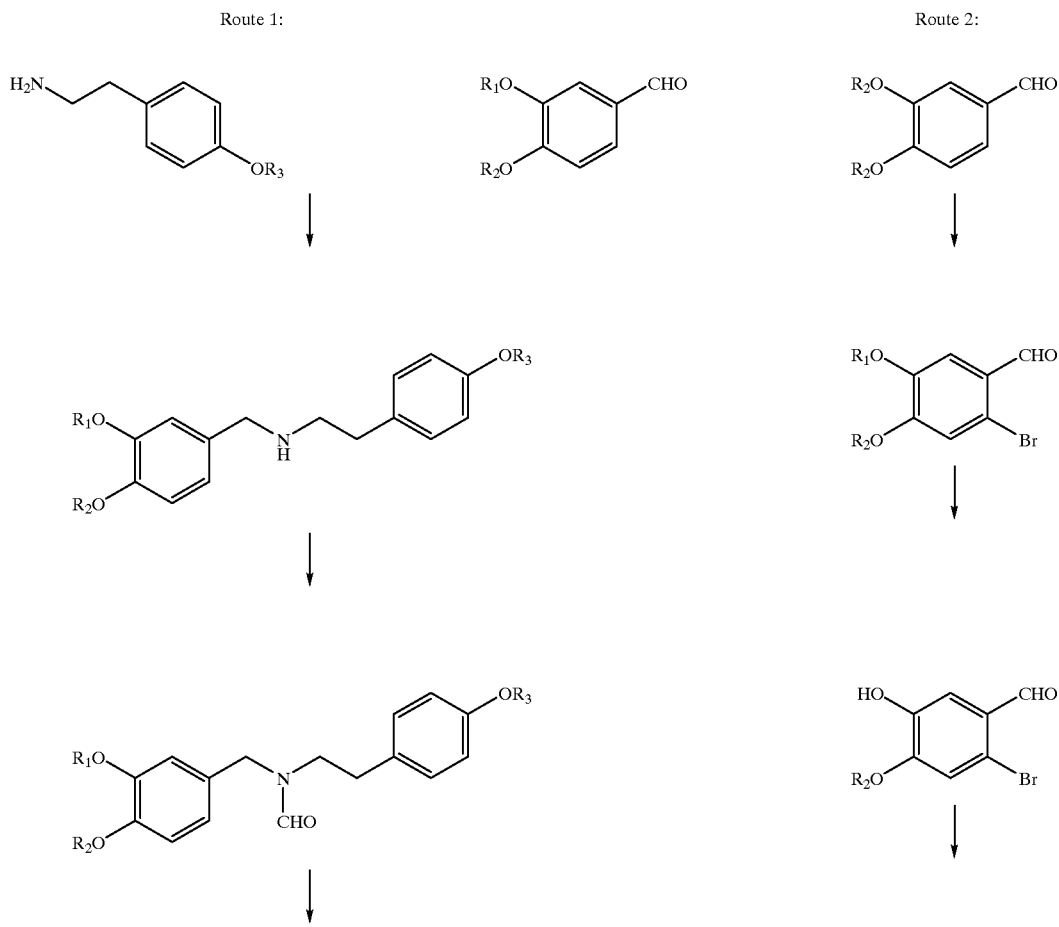

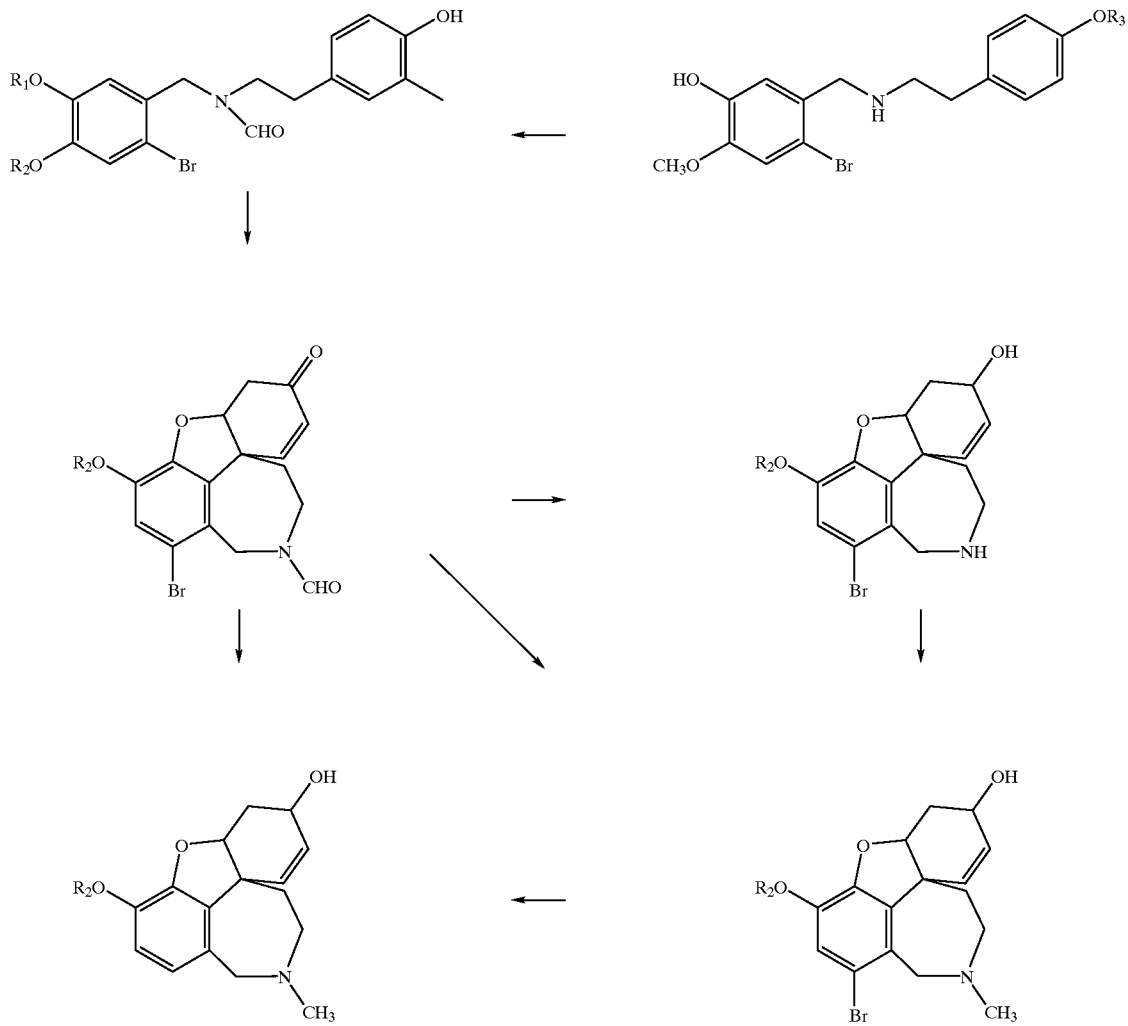
Reductions of Bromonarwedine—Overview
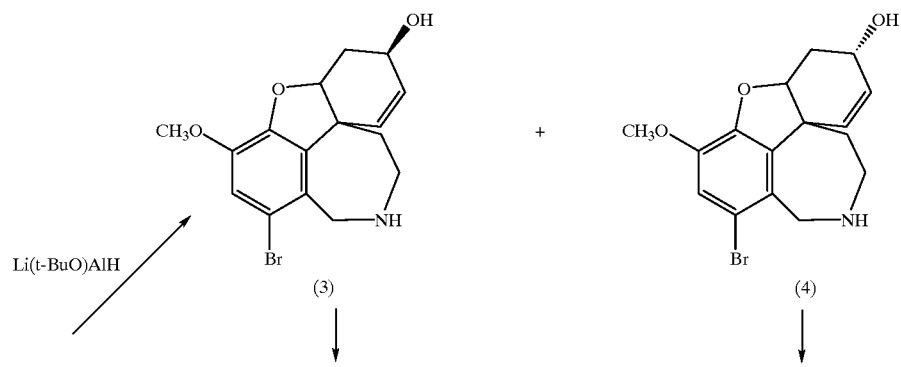

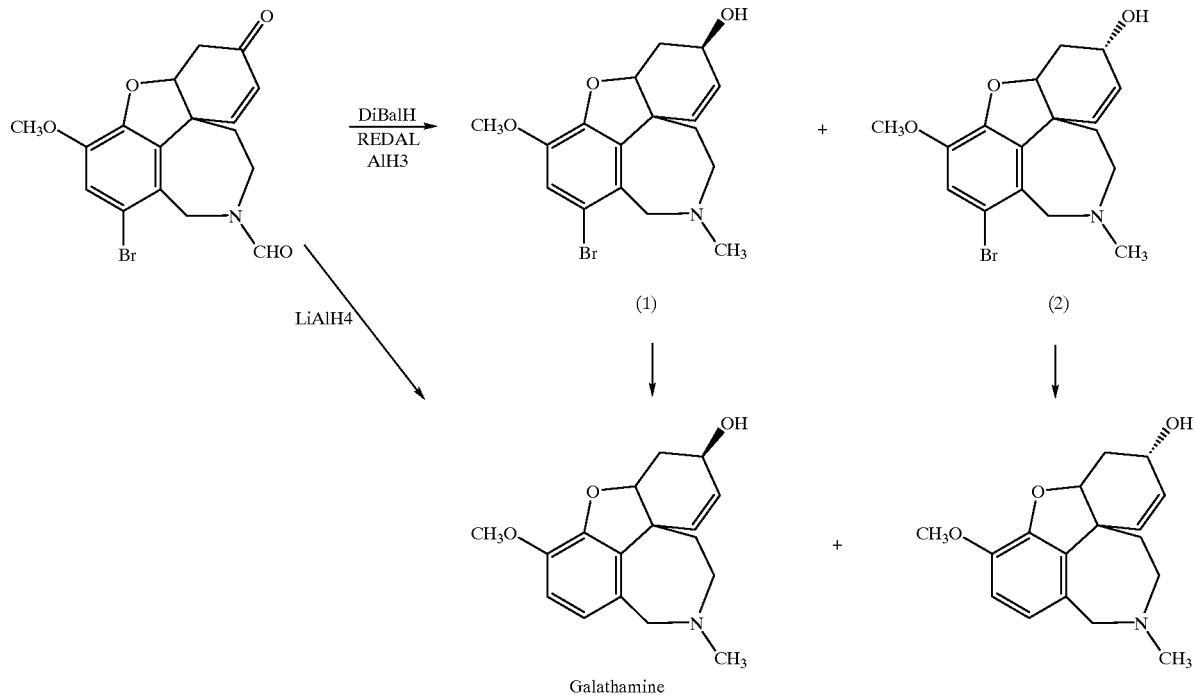
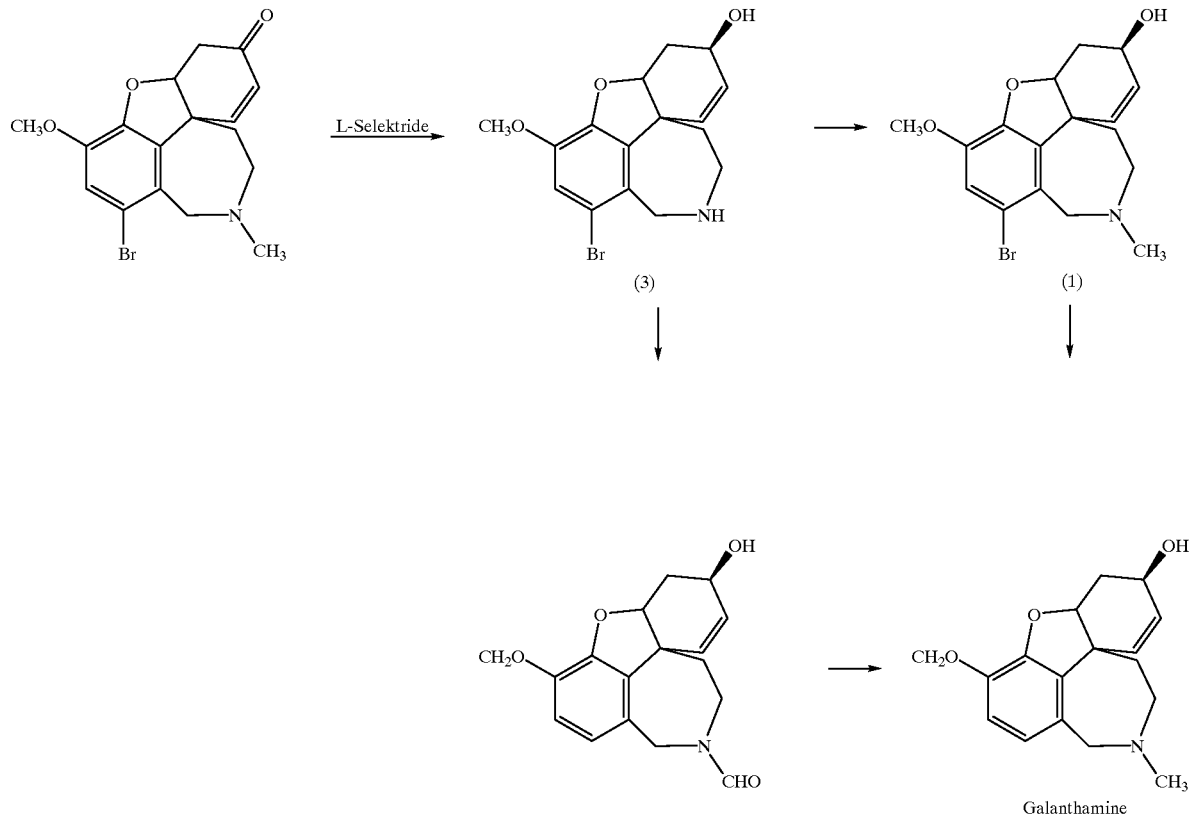
Reduction with L-Selektride

Chiral Separation of Galanthamine

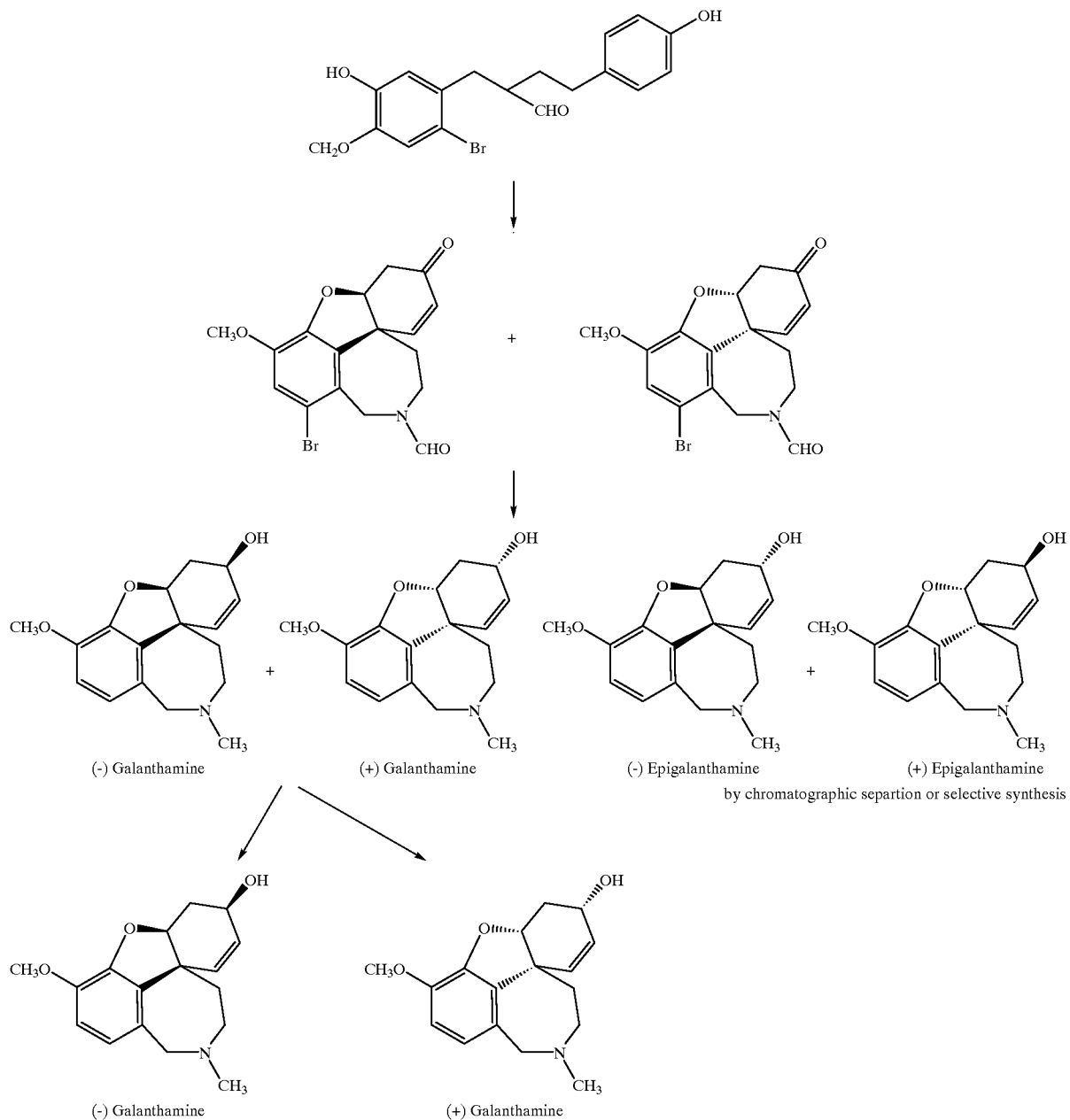

According to one variant of the process of the invention, narwedine can be obtained starting from the cyclized compound of the general formula (I) where $Y_1$, $Y_2$=O (ketone) via the introduction of a cyclic ketal as a protective group ($Y_1$, $Y_2$=substituted or unsubstituted cyclic ketal or thioketal, for example propylene glycol; O—$CH_2$—$CH_2$ ($CH_3$)—O), subsequent reduction with $LiAlH_4$ and splitting off of the ketal protective group. Racemic narwedine (or a compound of the general formula (I) in which $Y_1$, $Y_2$ are =O (ketone)) can be enriched by addition of catalytic amounts of (+)galanthamine or of (−)narwedine and (−)narwedine can be obtained with an enantiomeric purity of >98%.

The advantage of this variant of the invention is that the unwanted enantiomer can be converted into the desired enantiomer.

Racemic narwedine can be enriched to (+)narwedine in a similar manner by addition of catalytic amounts of (−)galanthamine or (+)narwedine. Enriched narwedine is converted into enantiomerically pure galanthamine in a good yield with L-Selektride, it being possible for either the free base or, directly, the hydrobromide to be obtained by appropriate working up. Galanthamine hydrobromide can be obtained with an enantiomeric content of >99% by crystallization of the hydrobromide. The content is determined by measurement of the optical rotation and by quantitative determination of the enantiomers by means of microcapillary electrophoresis in chiral electrolyte.

The abovementioned steps can be carried out generally and by way of example as follows:

7. Introduction of the protective group:

For introduction of a ketal protective group the compound of the general formula (I) where $Y_1$, $Y_2$ are =O (ketone), $X_1$ is Br and $R_1$ is CHO is heated at the reflux temperature in solvents, such as benzene, toluene or xylene, but chiefly toluene, together with 1 to 30 times the amount of diols, such as ethylene glycol or propylene glycol, or dithiols, such as 1,3-dithiopropane, in the presence of catalytic amounts of p-toluenesulfonic acid or concentrated sulfuric acid or other acids for several hours using a water separator. The mixture is subsequently cooled and the diol phase (dithiol phase) is separated off and extracted with toluene and the ketal (thioketal) obtained is isolated by evaporation of the toluene phases.

8. Reduction, splitting off of the protective group:

Purified or crude ketal (thioketal) of the general formula (I) (chiefly where $X_1$ is Br and $R_4$ is CHO) is converted into narwedine by reduction with $LiAlH_4$ and subsequent splitting off of the ketal group. For example, the propylene glycol ketal of the compound of the general formula (I) is dissolved in THF, 3 to 5 times the stoichiometric amount of $LiAlH_4$ are added and the mixture is heated at the reflux temperature for 12 hours. Any $X_1Br$ is thereby also converted into $X_1H$ and $R_4CHO$ is converted into $R_4CH_3$. Decomposition of the excess $LiAlH_4$ with $NH_4OH$, filtration and extraction with EtOAc gives the ketal-protected compound of the general formula (I) of the narwedine type. Heating the crude product in an acid, chiefly 2N hydrochloric acid, and rendering the mixture alkaline with $NH_4OH$ gives the compound of the general formula (I) of the narwedine type in a good yield (about 80%). If the mixture is stirred with $LiAlH_4$ at $-10°$ to $0°$ C. for 2 hours and then hydrolyzed with $NH_4OH$ and extracted with EtOAc, ketal-protected N-demethylbromonarwedine can be obtained. In a manner comparable to that of reduction with L-Selektride, a compound of the general formula (I) where $R_4$ is $CH_2$—OH is intermediately formed, and is decomposed during the hydrolysis to give the N-demethyl compound. By treatment in 2N HCl the ketal group can be split off and a compound of the demethyl-bromo-narwedine type can be obtained. Alkylation of the O-protected or unprotected compounds of the demethyl-bromo-narwedine type or introduction of an N-protective group and splitting off of any O-protective group present gives differently substituted narwedine of the general formula (I) where $Y_1$, $Y_2$=O (ketone), and where $R_4$ is substituted or unsubstituted alkyl, alkenyl, alkynyl, aryl or aralkyl or any protective group or quaternized compounds of the general formula (II). Debromination, for example with $Zn/CaCl_2$, gives N-substituted compounds of the narwedine type.

If a compound of the general formula (I) where $Y_1$, $Y_2$=ethylene glycol ketal is heated at 45–50° C. with $LiAlH_4$ in THF for 12 hours, correspondingly ketal-protected narwedine is formed. If the pressure is heated at the reflux temperature (65–68° C.) for 24 hours, the cyclic ketal structure opens up and a product where $Y_1$ is —$CH_2$—$CH_2$—OH and $Y_2$ is H is formed, but this can likewise be converted into a compound of the narwedine type by brief heating in an acid, chiefly 2N HCl.

It is interesting that the reduction with $LiAlH_4$ leads to demethyl-bromo-narwedine ketal at 0° C., to narwedine ketal at 45° C., to galanthamine hydroxyethyl ether at 70° C. over 48 hours and to narwedine at 45–70° C. with subsequent treatment with HCl (also splits the ketal).

Reduction of a ketal-protected compound of the general formula (I) where $X_1$ is Br and $R_4$ is CHO with $Zn/CaCl_2$ leads to reduction of the bromide, to splitting off to the ketal group but to retention of $R_4$ CHO.

9. Enrichment:

A racemic compound of the general formula (I) where $Y_1$, $Y_2$=O (ketone), $R_4$ is $CH_3$ is heated at the reflux temperature in a solvent such as water, methanol, ethanol, n-propanol, butanol, methylene glycol, ethylene glycol or mixtures of these solvents with 1 to 30% of triethylamine or similar bases, and optically pure compounds, for example (+)galanthamine or (−)narwedine, are added. For example, either (+)galanthamine or (−)narwedine are used for (−)narwedine, and for (+)narwedine, for example, (−)galanthamine or (+)narwedine are used and the mixture is cooled slowly in stages.

The mixture is preferably stirred at 40° C. for 1 to 14 days and then cooled to 0–20° C., and the optically enriched crystals which have precipitated out are isolated and an enantiomeric content of >98% is determined by means of microcapillary electrophoresis. Optical rotations of 405–407° C. (20° C., c=1/$CHCl_3$), for example, are achieved here for narwedine. Determination by means of microcapillary electrophoresis in chiral electrolytes gives an enantiomeric content of >98%.

10. Reduction:

The enantiomerically pure compound of the narwedine type ($Y_1$, $Y_2$=O, ketone) can be converted diastereoselectively into the enantiomerically pure compound of the galanthamine type ($Y_1$ or $Y_2$ is OH) with L-Selektride analogously to the instructions already given. Working up with aqueous HBr gives the corresponding galanthamine hydrobromide with an enantiomeric content of >99%, in a yield of 87–95% of theory.

11. Splitting off of bromide:

A compound of the general formula (I) where $X_1$ is Br is dissolved in 5 to 50 times the amount of a solvent, such as water, methanol, ethanol, n-propanol, iso-propanol, n-butanol or mixtures thereof, chiefly 70% of ethanol, 1 to 5 times the amount of zinc powder and 1 to 10 times the amount of $CaCl_2$ are added and the mixture is stirred. After on average about 1 to 2 hours, the solid is filtered off and the solution evaporated and chromatographed (silica gel 60, solvent for example acetone) to give 80 to 85% of debrominated product.

Compared with the method described in Lit. 24, it has been possible to improve the process such that a procedure on an industrial scale is possible. For example, the precursor is added in powder form to a preferably 1 molar solution of L-Selektride in THF at room temperature, the mixture is stirred for one hour, methanol is added and the mixture is evaporated. Taking up in ethanol (for example 5–30 times the amount) and acidification with aqueous KBr gives galanthamine hydrobromide in yields of 90 to 95% at an enantiomeric content of >99%.

The process variant described leads in some cases to novel compounds, or novel compounds are formed as intermediates. The novel compounds are:

21

Bromo-N-formyl-narwedine propylene glycol ketal (5)

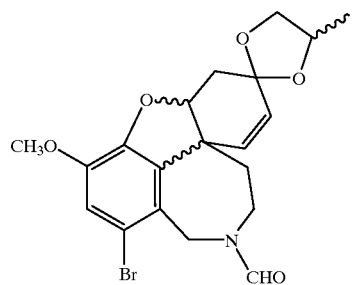
(5)

Narwedine propylene glycol ketal (6)

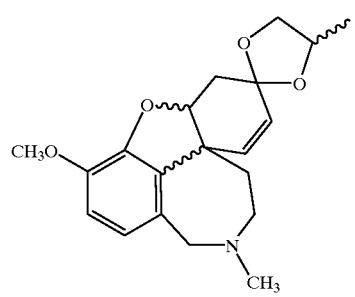
(6)

Bromo-N-formyl-narwedine ethylene glycol ketal (7)

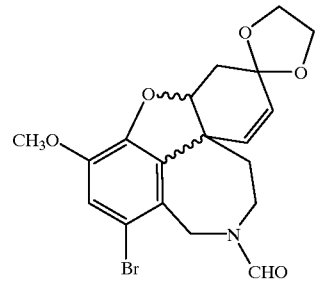
(7)

Narwedine ethylene glycol ketal (8)

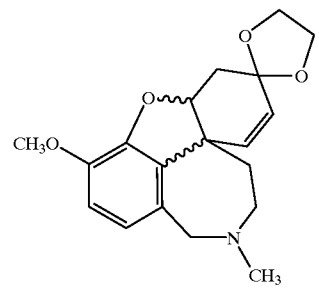
(8)

22

O-(2-Hydroxyethyl)galanthamine (9)

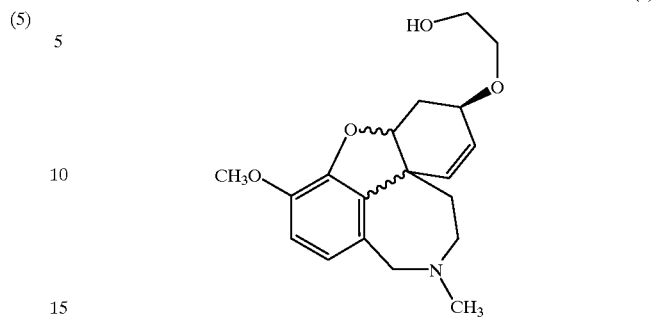
(9)

Bromo-N-demethyl-narwedine ethylene glycol ketal (10)

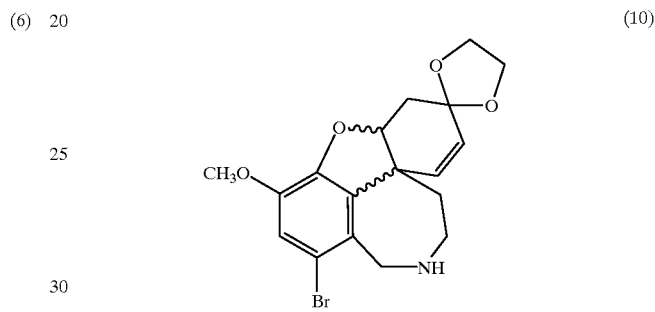
(10)

Bromo-N-benzyl-narwedine ethylene glycol ketal (11)

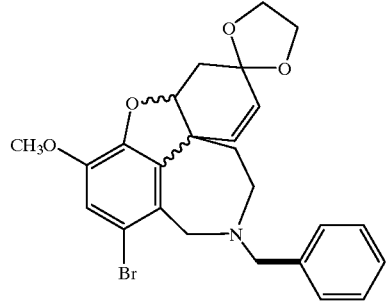
(11)

Bromo-N-demethylnarwedine (12)

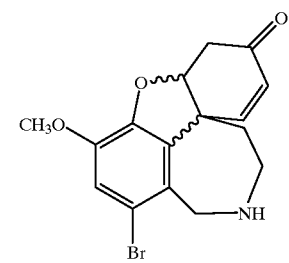
(12)

The numbers assigned to these compounds are also used in the reaction equations reproduced below.

Reaction Equations for Narwedine via Ketal-protected Bromoformylnarwedine
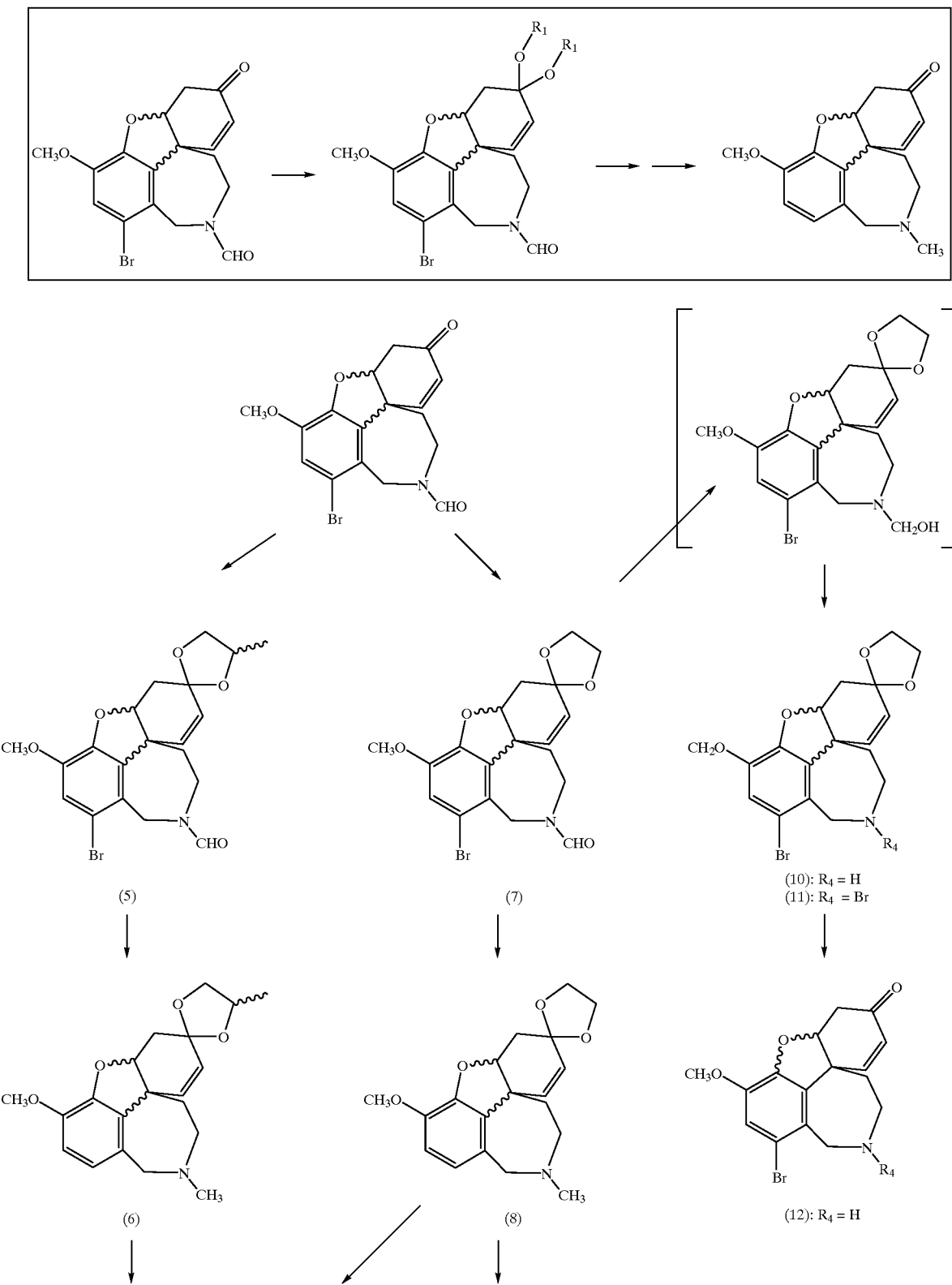

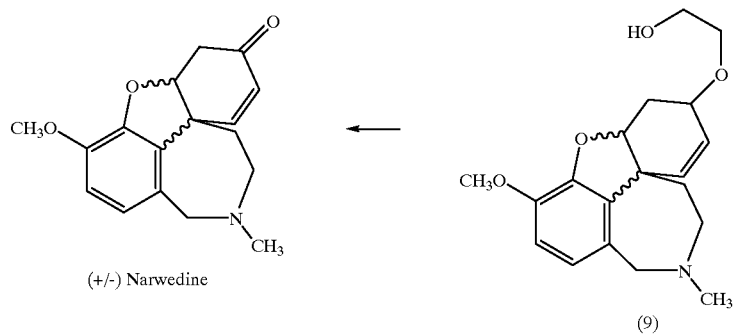
(+/−) Narwedine
-continued
(9)
Overall Overview of a Preferred Process of the Invention for the Synthesis of (−)galanthamine
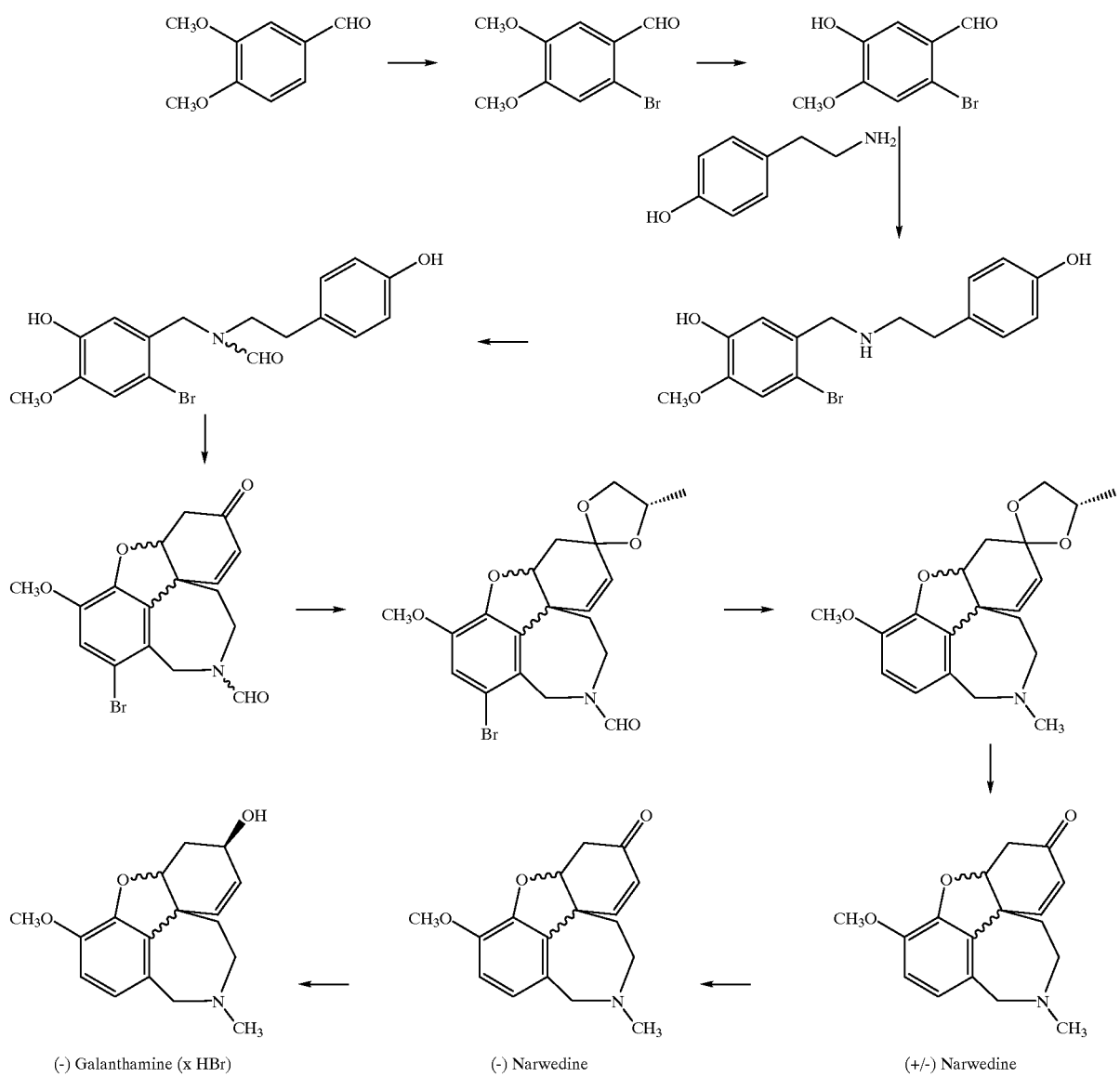

According to a further variant of the invention, the procedure used for preparing racemic compounds of the narwedine type is such that a compound of the general formula (Ia)

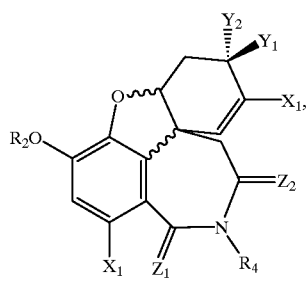

(Ia)

in which $R_2$, $R_4$, $X_1$ and $X_2$ have the meanings given in connection with the general formula (I), $Z_1$ and $Z_2$ =O, S or N and $Y_1$ and $Y_2$ are =O (ketone) is prepared by oxidative cyclization of a compound of the general formula (Va)

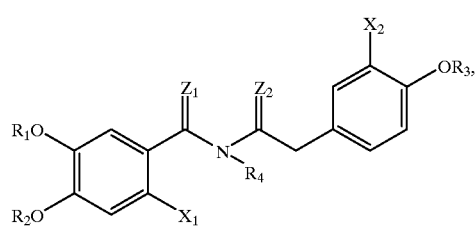

(Va)

in which $R_1$, $R_2$, $R_3$, $R_4$, $X_1$ and $X_2$ have the meanings given in connection with the general formula (V) and $Z_1$ and $Z_2$ are =O, S or N.

The product is subsequently converted, for example in a manner similar to stage 7.) described above, into a ketal or thioketal or cyclic ketal or cyclic thioketal, reduced with a reducing agent such as $LiAlH_4$ similar to stage 8.) described above, isolated as ketal or thioketal, or converted by preferably acidic hydrolysis into the corresponding compound of the narwedine type. The equation is given in the review "Synthese von Narwedin über Benzazepinion-Typ" (for: $Z_2=H_2$).

A by-product which can be formed in various concentrations as a result of alcoholysis is a compound of the formula (VI)

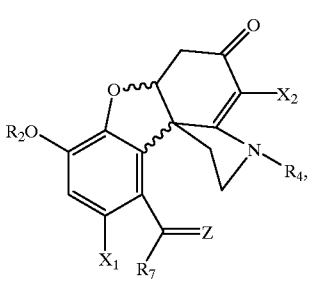

(VI)

in which $R_2$, $R_4$, $X_1$, $X_2$, $Z_1$ and $Z_2$ have the meanings stated in connection with the general formula (Ia) and $R_7$ corresponds to the alcohol or thiol used for preparing the ketal, for example —O—$CH_2CH(CH_3)$—OH (propylene glycol radical).

Synthesis of Narwedine by Way of Benzazepinone Type

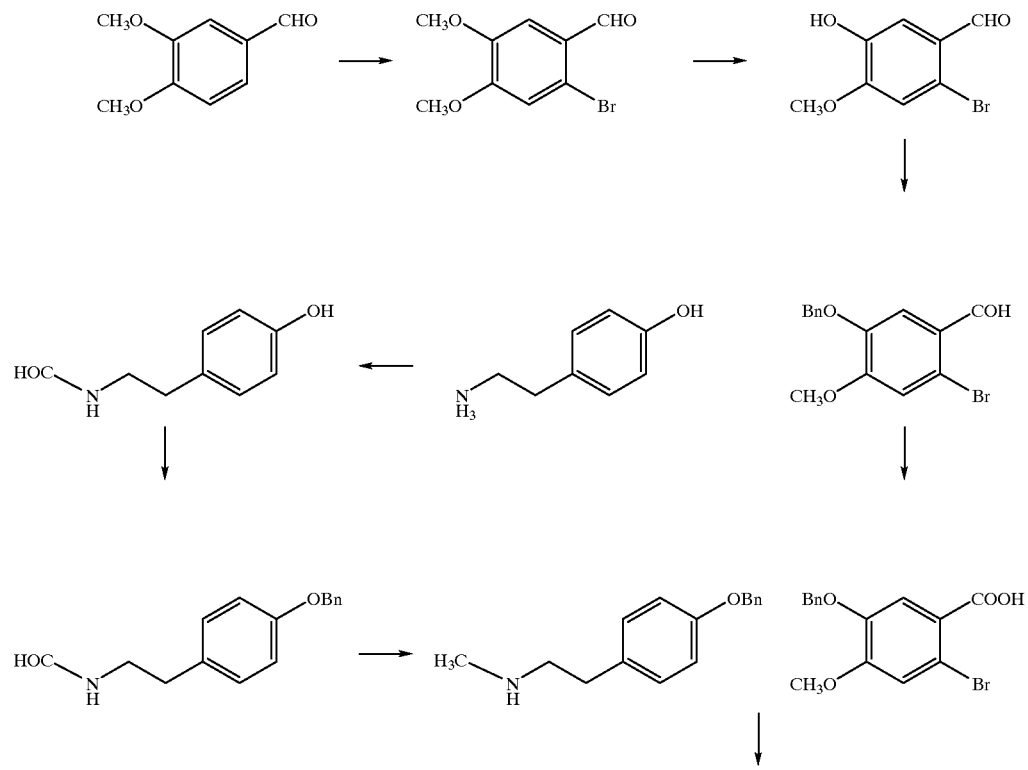

-continued

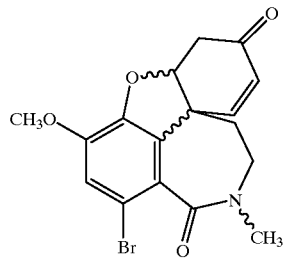
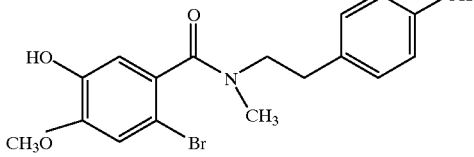

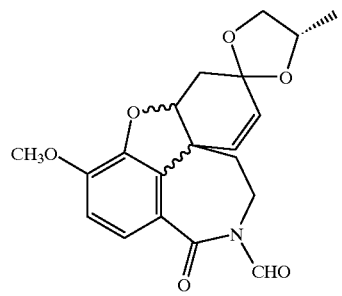
→
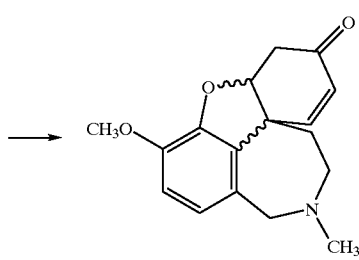

(+/−) Narwedine

The reduction of the compound of the general formula (Ia) in which $R_2$, $R_4$, $X_1$ and $X_2$ have the definitions given in connection with the general formula (I), $Z_1$ and $Z_2$=O, S, or N, and $Y_1$ and $Y_2$ are =O (ketone) with L-Selektride gives a compound of the formula (Ia) where $Y_1$=OH, $Y_2$=H.

The reduction of a compound of the formula (Ia) where $Y_1$, $Y_2$=O with LiAlH$_4$ gives a mixture of the galanthamine type ($Y_1$=OH, $Y_2$=H) and epigalanthamine type ($Y_1$=H, $Y_2$=OH) in a ratio of about 5:3, where $X_1$, $X_2$=Br are reduced to $X_1$, $X_2$=H and Z=O is reduced to Z=H$_2$.

The described process variant leads in part to novel compounds:

(13)

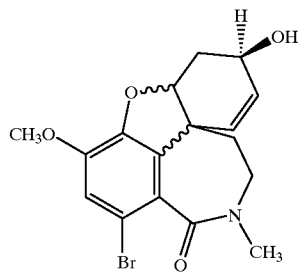

(14)

-continued

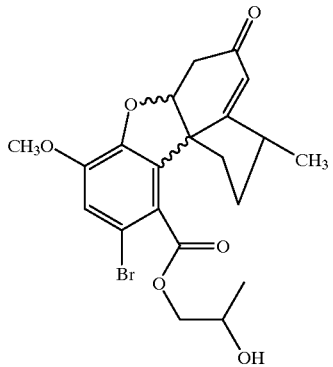

(15)

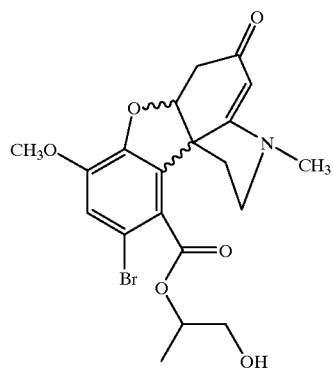

EXAMPLE 1

N-(4-hydroxyphenethyl)-(3-hydroxy-4-methoxy)benzylamine (general formula (V) where: $R_1=R_3=R_4=X_1=X_2=H$, $R_2=Me$)

217.5 g (1.43 mol) of isovanillin and 200 g (1.45 mol) of tyramine are suspended in 2.5 l of toluene/n-butanol (1:1) in a glass 5 l double-walled vessel and the suspension is heated to the reflux temperature, water being separated off. After 4 hours, the solvent is distilled off in vacuo, the residue is taken up in 2.5 l of methanol, and 25 g of $NaBH_4$ (0.66 mol) are added to the clear solution. The reaction mixture is stirred at 0° C. for 4 hours and the precipitate which has separated out is filtered off, washed with methanol and dried.

Yield: 332.3 g (85/1%)

Melting point: 176–178° C.

Molecular weight: $C_{16}H_{19}NO_3$: 273.32

EXAMPLE 2

N-(4-hydroxyphenethyl)-(6-bromo-3,4-dimethoxy)benzylamine (general formula (V) where $R_3=R_4=X_2=H$, $R_1=R_2=Me$, $X_1=Br$)

2.45 g (10 mmol) of 6-bromo-3,4-dimethoxybenzaldehyde, 1.37 g (10 mmol) of tyramine in 50 ml of toluene/n-butanol (1:1) are suspended in a 100 ml round-bottomed flask and the suspension is heated to the reflux temperature, water being separated off. After 3 hours, the solvent is distilled off in vacuo, the residue is taken up in 50 ml of methanol and 0.8 g of $NaBH_4$ is added to the clear solution. The reaction mixture is stirred at 0° C. for 4 hours, the solvents are distilled off in vacuo, the residue is taken up in 100 ml of $CH_2Cl_2$ and the organic phase is washed with twice 10 ml of water. The organic phase is dried over $Na_2SO_4$ and filtered and the solvent is removed in vacuo. The residue which remains is chromatographed over 150 g of silica gel with hexane:ethyl acetate=2:8.

Yield: 2.95 g (80.6%) of viscous oil

Molecular weight: $C_{17}H_{20}BrNO_3$: 366.23

EXAMPLE 3

N-(4-hydroxyphenethyl)-(4-methoxy-3-methoxymethoxy)benzylamine (general formula (V) where $R_1=MeOCH_2O$, $R_2=Me$, $X_1=X_2=X_3=X_4=R_3=R_4=H$)

0.83 g (4.2 mmol) of 4-methoxy-3-methoxymethoxybenzaldehyde [Lit. 16–17] and 0.55 g (4.0 mmol) of tyramine are suspended in 50 ml of toluene/n-butanol (1:1) in a 100 ml round-bottomed flask and the suspension is heated at the reflux temperature, water being separated off. After 4 hours, the solvent is distilled off in vacuo, the residue is taken up in 50 ml of methanol, and 0.35 g of $NaBH_4$ is added to the clear solution. The reaction mixture is stirred at 0° C. for 4 hours, the solvents are distilled off in vacuo, the residue is taken up in 100 ml of $CH_2Cl_2$ and the organic phase is washed with twice 10 ml of water. The organic phase is dried over $Na_2SO_4$ and filtered and the solvent is removed in vacuo. The residue which remains is chromatographed over 65 g of silica gel with ethyl acetate:methanol=7:3.

Yield: 1.12 g (83.4%) of viscous oil

Molecular weight: $C_{18}H_{23}NO_4$:317.37

EXAMPLE 4

N-(4-hydroxyphenethyl)-(6-bromo-3-hydroxy-4-methoxy)benzylamine (general formula (V) where $R_1=R_3=R_4=H$, $X_2=H$, $R_2=Me$, $X_1=Br$)

Method 1:

1.0 g (4.3 mmol) of 6-bromo-4-methoxy-3-hydroxybenzaldehyde [Lit. 18] and 0.6 g (4.3 mmol) of tyramine are suspended in 20 ml of toluene/n-butanol (1:1) in a 50 ml round-bottomed flask and the suspension is heated at the reflux temperature, water being separated off. After 90 minutes, the solvent is distilled off in vacuo, the residue is taken up in 20 ml of methanol, and 0.33 g of $NaBH_4$ is added to the clear solution. The reaction mixture is stirred at 0° C. for 4 hours, the solvents are distilled off in vacuo, the residue is taken up in 50 ml of $CH_2Cl_2$ and the organic phase is washed with twice 10 ml of water. The organic phase is dried over $Na_2SO_4$ and filtered and the solvent is removed in vacuo. The residue which remains is chromatographed over 60 g of silica gel with ethyl acetate:methanol=97:3→95:5

Yield: 1.43 g (93.8%)

Method 2:

53.38 g (231 mmol) of 6-bromo-4-methoxy-3-hydroxybenzaldehyde [Lit. 18] and 31.7 g (231 mmol) of tyramine are suspended in 530 ml of toluene/n-butanol (1:1) in a 1 l round-bottomed flask and the suspension is heated at the reflux temperature, water being separated off. After 90 minutes, the solvent is distilled off in vacuo, the residue is taken up in 350 ml of methanol, and 12 g of $NaBH_4$ are added to the suspension. The reaction mixture is stirred at 0° C. for 1 hour and added dropwise to 3 l of ice-water. After the mixture has been stirred for 30 minutes, the product which has precipitated out is filtered off, washed twice with water and dried in a vacuum drying cabinet at 60° C.

Yield: 70.2 g (86.3%)

Melting point: 122–125° C.

Molecular weight: $C_{16}H_{18}BrNO_3$.352.21

IR/KBr: 655.76 w; 800.45 m, 824.97 m; 1022.56 m; 1165.88 m; 1245.88 s; 1409.83 s; 1448.40 s; 1510.79 s; 1554.48 s; 3200–3370 br.

$^1$H-NMR (DMSO-$d_6$): 7.0–6.60 (m, 6 H); 6.73 (m, 2H); 3.77 (s, 3H); 2.75–2.58 (m, 4H); 2.88 (s, 2 OH). $^{13}$C-NMR ($CDCl_3$+DMSO-$d_6$): 155.46 s, 147.28 s, 145.95 s, 130.56 s, 129.68 s, 129.12 2 d, 116.93 d, 115.61 d, 114.99 2 d, 110.95 s, 55.85 q, 51.76 t, 50.16 t, 34.50 t.

EXAMPLE 5

N-(4-hydroxyphenethyl)-(4methoxy-3-t-butyl-carbonyloxy)benzylamine (general formula (V) where $R_1mMe_3CCO$, $R_2=Me$, $X_1=X_2=R_3=R_4=H$)

3.63 g (16.5 mmol) of (4-methoxy-3-t-butyl-carbonyloxy)benzaldehyde and 2.06 g (15 mmol) of tyramine are suspended in 32 ml of toulene/n-butanol=1:1 in a 50 ml round-bottomed flask and the suspension is heated at the reflux temperature, water being separated off. After 3 hours, the solvent is distilled off in vacuo, the residue is taken up in 32 ml of methanol, and 1.32 g of $NaBH_4$ are added to the clear solution. The reaction mixture is stirred at 0° C. for 4 hours, the solvents are distilled off in vacuo, the residue is taken up in 50 ml of $CH_2Cl_2$ and the organic phase is washed with twice 10 ml of water. The organic phase is dried over $Na_2SO_4$ and filtered and the solvent is removed in vacuo. The residue which remains is chromatographed over 140 g of silica gel with ethyl acetate:methanol=9:1→8:2.

Yield: 1.7 g (28.8%) of viscous oil

Molecular weight: $C_{21}H_{27}NO_4$:357.43

EXAMPLE 6

N-formyl-N-(4-hydroxyphenethyl)-(3-hydroxy-4-methoxy)benxylamine (general formula (V) where: $R_1=R_3=X_1=X_2=H$, $R_2=Me$, $R_4=CHO$)

370 g (1.35 mmol) of compound 5 ($R_1=R_3=R_4-X_1=X_2=H, R_2=Me$), 5 l of technical grade dioxane and 370 ml of technical grade DMF are initially introduced into a 10 l three-necked flask (dropping funnel, reflux condenser, bubble counter, gas inlet tube). The dropping funnel is filled with a mixture of 1100 ml (13.66 mol) of HCOOEt and 10 ml of HCOOH, and the suspension is stirred magnetically under argon and heated to the boiling point. The internal temperature rises up to 100 to 103° C., the suspension becoming homogeneous. The solution from the dropping funnel is added to this solution in the course of 20 to 30 minutes. The internal temperature thereby drops to 87 to 89° C. The reaction mixture, which has become cloudy, is stirred at the reflux temperature for 4 hours. The solvent is removed in vacuo and 8 l of ice-water are added to the residue in portions. The crystals which are precipitated out are filtered off, washed three times with 2 l of water and dried in vacuo for 12 hours.

Yield: 360.5 g (88.6%)
Melting point: 144 to 148° C.
Molecular weight: $C_{17}H_{19}NO_4$:301.33

EXAMPLE 7

N-formyl-N-(4-hydroxyphenethyl)-(6-bromo-3,4-dimethoxy)benzylamine (general formula (V) where: $R_3=X_2=H$, $X_1=Br$, $R_1=R_2=Me$, $R_4=CHO$)

A mixture of 4.53 g (12.2 mmol) of 5 ($R_3=R_4=X_2=H, X_1=Br, R_1=R_2=Me$), 100 ml of technical grade dioxane, 10.0 ml (122.0 mmol) of HCOOEt and 0.1 ml of HCOOH is boiled under reflux in a 250 ml three-necked flask (dropping funnel, reflux condenser, bubble counter, gas inlet tube). After 68 hours, the solvent is removed in vacuo and the residue is crystallized from 40 ml of MeOH.

Yield: 3.61 g (75%)
Melting point: 160 to 162° C.
Molecular weight: $C_{18}H_{20}BrNO_4$:394.24

EXAMPLE 8

N-formyl-N-(4-hydroxyphenethyl)-(4-methoxy-3-t-butylcarbonyloxy)benzylamine (general formula (V) where $R_1=Me_3CCO$, $R_2=Me$, $X_1=X_2=R_3=H$, $R_4=CHO$)

A mixture of 1.7 g (4.7 mmol) of the compound of the formula (V) $R_1=Me_3CCO$, $R_2=Me$, $X_2=X_2=R_2=R_4=H$), 7.5 ml of technical grade dioxane, 7.5 ml of HCOOEt and one drop of HCOOH is boiled under reflux in a 500 ml three-necked flask. After 15 hours, the solvent is removed in vacuo and the residue is chromatographed on 30 g of $SiO_2$ with AcOEt.

Yield: 1.5 g (81.8%) of an oil
Molecular weight: $C_{22}H_{27}NO_5$:385.44
$^1$H-NMR (CDCl$_3$): 8.20 and 7.80 (2s, 1 H); 7.16–6.80 (m, 7H); 4.30 (d, 2 H); 3.78 (s, 3 H; 3.35 (m, 2 H); 2.70 (m, 2 H); 1.38 (s, 9 ).
$^1$H-NMR (CDCl$_3$): 8.20 and 7.80 (2s, 1 H); 7.16–6.80 (m, 7H); 4.30 (d, 2 H); 3.78 (s, 3 H; 3.35 (m, 2 H); 2.70 (m, 2 H); 1.38 (s, 9 H).
$^{13}$C-NMR (CDCl$_3$): 176.69 s; 163.24 and 162.90 d; 155.36 and 154.99 s; 150.99 and 150.70 s; 140.35 and 140.18 s; 129.67 to 112.30 m; 55.85 q; 50.94 and 48.46 t; 44.60 and 43.61 t; 38.94 s; 33.60 and 32.24 t; 27.05 3 q.

EXAMPLE 9

N-formyl-N-(4-hydroxyphenethyl)-(6-bromo-3-hydroxy-4-methoxy)benzylamine (general formula (V) where $R_1=R_3=X_2=H$, $X_1=Br$, $R_2=Me$, $R_4=CHO$)

Method 1:

A mixture of 27 g (76.6 mmol) of the compound (V) ($R_1=R_3=R_4=X_2=H, X_1=Br, R_2=Me$), 300 ml of technical grade dioxane, 30.0 ml (37.2 mmol) of HCOOEt and 0.1 ml of HCOOH is boiled under reflux in a 500 ml three-necked flask (dropping funnel, reflux condenser, bubble counter, gas inlet tube). After 72 hours, the solvent is removed in vacuo and the residue is crystallized from 50 ml of chloroform.

Yield: 23.95 g (82.3%)

Method 2:

300 g of the compound (V) ($R_1=R_3=X_1=X_2=H, R_2=Me, R_4=CHO$) were dissolved in 2000 ml of anhydrous ethanol and 2000 ml of methylglycol (H$_2$O<0.1%) by heating to 40° C., the solution was then cooled to −20° C. and 14 ml of bromine in 1000 ml of ethanol/methylglycol (1:1) were added dropwise in the course of 15 minutes such that the temperature did not exceed −20° C. The mixture was then stirred at −20° C. for 30 minutes and the solution was then concentrated to about 1000 ml and poured onto 30 l of ice-water with vigorous stirring. The mixture was stirred at 0° C. for 4 hours, the solid was filtered off with suction and the colorless, crystalline substance was dried in vacuo (60° C.).

Yield: 370.2 g (96% of theory); content (HPLC) 82%
Melting point: 162 to 164° C.
Molecular weight: $C_{17}H_{18}BrNO_4$:380.22

EXAMPLE 10

N-formyl-N-(4-hydroxyphenethyl)-(4-methoxy-3-methoxymethoxy)benzylamine (general formula (V) where $R_1=MeOCH_2O$, $R_2=Me$, $X_1=X_2=R_3=H$, $R_4=CHO$)

A mixture of 4.9 g (15.4 mmol) of the compound (V) ($R_1=MeOCH_2O, R_2=Me, X_1=X_2=R_3=R_4=H$), 60 ml of HCOOEt and one drop of HCOOH is boiled under reflux in a 50 ml three-necked flask (dropping funnel, reflux condenser, bubble counter, gas inlet tube). After 18 hours, the solvent is removed in vacuo and the residue is crystallized from AcOEt/hexane.

Yield: 3.95 g (74%)
Melting point: 102 to 104° C.
Molecular weight: $C_{19}H_{23}NO_5$:345.38
$^1$H-NMR (CDCl$_3$): 8.23 and 7.83 (2 s, 1 H); 7.05 to 6.70 (m, 7 H); 5.20 (s, 2 H); 4.46 and 4.28 (2 s, 2 H); 3.87 (s, 3 H); 3.52 (s, 3 H); 3.38 (m, 2 H); 2.70 (m, 2 H).
$^{13}$C-NMR (CDCl$_3$): 163.20 and 162.86 d; 155.41 and 155.05 s; 149.53 and 149.30 s; 146.53 and 146.33 s; 129.66 and 129.59 s; 129.52 d; 128.56 and 128.02 s; 122.40 d; 121.64 d; 116.71 d; 115.88 d; 115.60 and 115.33 d; 11.75 d; 95.39 t; 56.13 q; 55.79 q; 51.44 and 48.62 t; 45.10 and 43.71 t; 33.72 and 32.27 t.

EXAMPLE 11

4 $a$,5,9,10,11,12-hexahydro-1bromo-3-methoxy-11-formyl-6H-benzofuro [3 $a$,3,2-ef] [2]benzazepin-6-one (general formula (I) where: $R_2=Me$, $R_4=CHO$, $X_1=Br$, $X_2=H$, $Y_1,Y_2=$))

120 g (0.316 mol) of finely powdered compound (V) ($R_1=R_3=X_2=H, X_1=Br, R_2=Me, R_4=CHO$) are added all at once to a suspension of 16 l of toluene, 600 g of $K_3[Fe(CN)_6]$ and 2 l of 10% strength $K_2CO_3$ solution at 70° C. The reaction mixture is then stirred intensively at the same temperature for 30 minutes, with a homogenizer switched on, an insoluble polymer precipitating out. The reaction mixture is filtered, the organic phase is dried over $Na_2SO_4$ and filtered and the solvent is removed in vacuo.

Yield: 59.6 g (49.9%).

If precursor prepared according to Example 9, method 2 is employed for the cyclization, a by-product of the general formula (I) with $R_2=CH_3$, $X_1=X_2=Br$, $R_4=CHO$; $Y_1$, $Y_2=O$ was obtained in a 6% yield after separation by means of column chromatography (silica gel 60, $CHCl_3$/MeOH (1–5%)).

$^1$H-NMR ($CDCl_3$): 8.23 (d, 1H), 7.30 (s, 1H), 6.98 (s, 1H), 5.85–3.95 (m, 3H), 4.70 (s, 1H), 3.80 (s, 3H), 3.35 (m, 2H), 2.95 (m, 1H), 2.15 (m, 2H). $^{13}$C-NMR($CDCl_3$+DMSO $d_6$): 185.31 and 185.25 s, 162.43 and 161.43 d; 147.12 and 146.84 s; 144.61 and 144.37 s; 142.33 and 141.97 d, 129.27 and 129.13 s, 126.62 and 126.40 s, 123.40 and 123.25 s, 116.67 and 116.46 d, 114.27 and 112.74 s, 87.00 and 86.86 d, 56.01 q, 52.38 and 51.55 s, 46.18 and 45.80 t, 40.58 t, 37.68 and 36.86 t, 34.26 t.

EXAMPLE 12

(4α,6β)-4 a, 5,9,10,11,12-hexahydro-3methoxy-11-methyl-6H-benzofuro [3 a, 3,2,-ef] [2]benzazepin-6-ol (galanthamine)

(general formula (I) where: $r_2=R_4=Me$, $X_1=X_2=Y_2=H$, $Y_1=OH$)

Method 1:

4.6 g (121.21 mmol) of $LiAlH_4$ in 80 ml of absolute THF are initially introduced into a 1 1 three-necked flask and are cooled to 0° C. 7.36 g (19.47 mmol) of the compound (V) ($R_1=H$, $R_4=CHO$, $X_1=Br$, $X_2=H$, $Y_1,Y_2=$)) in 460 ml of absolute THF are added dropwise to this suspension in the course of 5 minutes, with vigorous stirring, and the mixture is stirred at 0° C. for 1 hour and boiled under reflux for 21 hours. The reaction mixture is then transferred to a 1 1 one-necked flask and cooled to 0° C., excess $LiAlH_4$ is destroyed with a few drops of $H_2O$ and the solvent is removed in vacuo. $H_2$) is added to the residue and the pH is brought to 1 with 2N HCl solution. The reaction solution is shaken and warmed up until the precipitate has dissolved. The pH is then brought to pH 9 with 2N NaOH, ethyl acetate is added to the cloudy solution, the mixture is shaken thoroughly and the precipitate which has separated out is filtered off. The organic phase is separated off and the aqueous phase is extracted with ethyl acetate. The combined organic phases are dried over $Na_2SO_4$ and filtered and the solvent is removed in vacuo. Purification of the residue by chromatography (300 g of $SiO_2$, with $CHCl_3$:MeOH= 97:3→95:5) gives colorless crystals.

Yield: 2.23 g (40.03%)

Method 2:

A solution of 365 mg (1.0 mmol) of the compound (I) ($R_2=R_4=Me$, $X_1=Br$, $X_2=Y_2=H$, $Y_1=OH$) in 4 ml of anhydrous THF is added dropwise to a suspension of 240 mg (6.3 mmol) of $LiAlH_4$ in 4 ml of absolute THF at 0° C., and the mixture is stirred at room temperature for 1 hour and then at the reflux temperature for 23 hours. The reaction mixture is now cooled to 0° C., excess reducing agent is destroyed with $H_2O$ and the mixture is diluted with 50 ml of ethyl acetate and 50 ml of concentrated $NH_4OH$. After shaking, the precipitate which has separated out is filtered [sic], the organic phase is separated and the aqueous phase is washed with ethyl acetate. The combined organic phases are dried over $Na_2SO_4$ and filtered and the solvent is removed in vacuo. Purification of the residue by chromatography (25 g of $SiO_2$, $CHCl_3$:MeOH=99:1→96:4) gives 140 mg (49%) of the compound (I) ($R_2=R_4=Me$, $X_1=X_2=Y_2=H$, $Y_1=OH$).

Method 3:

1.0 ml of HCOOH is added dropwise to a suspension of 100 mg (0.27 mmol) of the compound (I) ($R_2=R_4=Me$, $X_1=Br$, $X_2=H=Y_2=H$, $Y_1=OH$) and 10 mg of 10% strength Pd/C in 3 ml of $Et_3N$. After, the mixture has been stirred at the reflux temperature for 2.5 hours, the Pd/C is filtered off through Celite, the solvent is removed in vacuo and the residue is taken up in $CH_2Cl_2$. The organic solution is washed twice with saturated $NH_4Cl$ solution and once with $H_2O$ and dried with $Na_2SO_4$ and the solvent is evaporated off in vacuo. The residue is separated by means of column chromatography (9 g of $SiO_2$, $CHCl_3$: MeOH=95.5).

Yield: 62 mg (79%) of the compound (I) ($R_2=R_4=Me$, $X_1=X_2=Y_2=H$, $Y_1=OH$)

Melting point: 119 to 121° C.

Molecular weight $C_{17}H_{21}NO_3$:287.34

EXAMPLE 13

(4α,6β)-4 a, 5,9,10,11,12-hexahydro-1-bromo-3-methoxy-11-methyl-6H-benzofuro [3 a, 3,2-ef] [2]benzazepin-6-ol (bromogalanthamine)

(general formula (I) where: $R_2=R_4=Me$, $X_1=Br$, $X_2=Y_2=H$, $Y_1=OH$) and (4α,6α)-4 a,5,9,10,11,12-hexahydro-1-bromo-3-methoxy-11methyl 6H-benzofuro [3 a, 3,2-ef] [2]benzazepin-6-ol (epibromogalanthamine)

(general formula (I) where: $R_2=R_4=Me$, $X_1=Br$, $X_2=Y_1=H$, $Y_2=OH$)

10 ml (36 mmol) of 1.5M DiBal-H solution in toluene is added dropwise to a suspension of 8.0 g (21 mmol) of the compound (V) ($R_2=Me$, $R_4=CHO$, $X_1=Br$, $X_2=H$, $Y_1,Y_2=O$) in 150 ml of toluene at 0° C. The reaction is stirred at room temperature for 1 hour, the residual reducing agent is destroyed with $H_2O$, and 12 ml of concentrated $NH_4OH$ are then added. After the mixture has been stirred at room temperature for 20 minutes, the material which has precipitated out if filtered off, the organic phase is separated off and the aqueous phase is washed with 50 ml of toluene. The combined organic phases are dried over $Na_2SO_4$ and filtered and the solvent is removed in vacuo. The residue (7.7 g) is separated by means of column chromatography.

Yield: 3.2 g (45.1%) of the compound (I) where ($R_2=R_4=Me$, $X_1=Br$, $X_2=Y_2=H$, $Y_1=OH$) and 0.8 g (20.7%) of the compound (I) ($R_2=R_4=Me$, $X_1=Br$, $X_2=Y_1=H$, $Y_2=OH$), Data for bromogalanthamine (compound (I) where $R_2=R_4=Me$, $X_1=Br$, $X_2=Y_2=H$, $Y_1=OH$):

Molecular weight: $C_{17}H_{19}BrNO_3$:365.23

IR(KBr): 689.03 m; 778.57 m; 839.37 m; 989.86 m; 1050.66 s; 1212.43 s; 1279.87 s; 1434.08 s; 14.72 s; 1613.99 s; 2667.39 m; 3370 to 3778br $^1$H-NMR ($CDCl_3$): 6.9 (s, 1 H); 6.06 (m, 2 H); 4.60 (d, 1 H); 4.15 (t, 1 H); 3.92 (d, 1 H); 3.82 (s, 3 H); 3.24 (m, 1 H); 2.98 (dt, 1 H); 2.68 (dd, 1 H); 2.42 (s, 3 H); 2.05 (m, 2 H); 1.60 (dt, 1 H).

$^{13}$C-NMR ($CDCl_3$): 145.32 s; 144.00 s, 133.96 s; 127.95 d; 127.68 s; 126.51 d; 115.61 d; 114.22 s; 88.56 d; 61.58 d; 58.56 t; 55.95 q; 53.26 t; 48.56 s; 42.06 q; 33.47 t; 2969 t.

Data for epibromogalanthamine (compound (I) where $R_2=R_4=Me$, $X_1=Br$, $X_2=Y_1=H$, $Y_2=OH$):

Molecular weight: $C_{17}H_{19}BrNO_3$:365.23

IR(KBr): 667:95 w; 752 m; 836.68 m; 1040.31 s; 1208.39 s; 12.82 m; 1435.25 m; 1485.72 m; 1512.94 w; 1558.27 w; 1615.19 m; 1667.14 w; 2943.24 w; 3360 to 3575br.

$^1$H-NMR ($CDCl_3$): 6.85 (s, 1 H); 5.96 (AB, 2H); 4.69 (m, 2 H); 4.28 (d, 1 H); 3.90 (d, 1 H); 3.83 (s, 1H); 3.25 (m, 1 H), 2.95 (m, 1 H); 2.85 (dt, 1 H); 2.36 (s, 3 H); 2.15 (td, 1 H); 1.69 (m, 2 H).

$^{13}$C-NMR ($CDCl_3$+DMSO-$d_6$): 145.84 s; 143.49 s; 133.89 s; 133.14 d; 126.12 s; 124.35 d; 115.04 s; 113.01 s; 88.26 d; 61.10 d; 57.44 t; 55.58 q; 52.84 t; 47.86 s; 41.20 q; 33.35 t; 31.43 t.

EXAMPLE 14

(4α, 6α) -4a,5,9,10,11,12- hexahydro-3-methoxy-11-methyl-6H-benzofuro[3a,3,2-ef] [2]benzazepin-6-ol (epigalanthamine)
(general formula (I) where: $R_2=R_4=Me$, $X_1=X_2=Y_1=H$, $Y_2=OH$)

A solution of 365 mg (1.0 mmol) of the compound (I) ($R_2=R_4=Me$, $X_1=Br$, $X_2=Y_1=H$, $Y_2=OH$) in 4 ml of absolute THF is added dropwise to a suspension of 240 mg (6.3 mmol) of $LiAlH_4$ in 4 ml of anhydrous THF at 0° C. and the mixture is stirred at room temperature for 1 hour and then at the reflux temperature for 23 hours. The reaction mixture is now cooled to 0° C., excess reducing agent is destroyed with $H_2O$ and the mixture is diluted with 50 ml of ethyl acetate and 50 ml of ethyl acetate [sic] and 50 ml of concentrated $NH_4OH$. After shaking, the precipitate which has separated out is filtered [sic], the organic phase is separated off and the aqueous phase is washed with ethyl acetate. The combined organic phases are dried over $Na_2SO_4$ and filtered and the solvent is removed in vacuo. The residue is separated by means of column chromatography (25 g of $SiO_2$), $CHCl_3:MeOH=99.1\rightarrow96:4$).

Yield: 140 mg (49%) of 1 ($R_2=R_4=Me$, $X_1=X_2=Y_1=H$, $Y_2=OH$)

Melting point: 199 to 201° C.

Molecular weight: $C_{17}H_{21}NO_3$:287.34

EXAMPLE 15

(4α, 6β) -4a,5,9,10,11,12-hexahydro-1-bromo-3-methoxy-6H-benzofuro[3a,3,2-ef] [2]benzazepin-6-ol (N-demethyl-bromogalanthamine)
(general formula (I) where: $R_2=Me$, $X_1=Br$, $R_4=X_2=Y_2=H$, $Y_1=OH$)

100 ml (100 mmol) of a 1 M solution of L-Selektride are added dropwise to a suspension of 10 g (26.4 mmol) of (1) ($R_2=Me$, $R_4=CHO$, $X_1=Br$, $X_2=H$, $Y_1=Y_2=O$) in 200 ml of THF at 0° C. in the course of 30 minutes. After the mixture has been stirred at 0° C. for 60 minutes, the complex formed with the reagent is destroyed with $H_2O$, and 100 ml of 25% strength $NH_4OH$ solution are added to the reaction mixture. After the mixture has been stirred at room temperature for 30 minutes, the solvent is concentrated to half in vacuo, the mixture is transferred into a shaking funnel, 100 ml of 25% strength $NH_4OH$ solution are added and the mixture is extracted with 3×200 ml of $CH_2Cl_2$. The combined organic phases are dried with $Na_2SO_4$ and filtered and the solvent is evaporated off in vacuo. Purification of the residue by chromatography (650 g of $SiO_2$ silica gel $ClCl_3:MeOH=95:5\rightarrow9:1$) gives a colorless foam.

Yield: 7.3 g (75.8%)

$C_{16}H_{18}BrNO_3$:352:21

IR(KBr): 748.19 m; 793.11 m; 828.59m; 927.62w; 991.65w; 1058.8s; 1214.79s; 1281.61s; 14.29s; 1488.49s; 1571.11w; 1616.51s; 2912.36s; 3280 to 3420br.

UV(MeOH): $\lambda_{max}$:225.0 and 297.5 nm.

$^1$H—NMR ($CDCl_3$): 6.85 (s, 1H); 6.02 (AB, 2 H); 4.53 (s, 1H); 4.81 and 4.48 (AB, 2H); 4.10 (m, 1H); 3.78 (s, 3H); 3.22 (m, 2H); 2.63 (dd, 1H); 2.29 (s, br, 2H); 2.00 (m, 1H); 1.78 (m, 2H).

$^{13}$C—NMR ($CDCl_3$): 145.79s; 143.96s; 134.06s; 131.64s; 127.87d; 126.83d; 115.46d; 113.02s; 88.44d; 61.67d; 56.04q; 52.65t; 49.23s; 46.59t; 39.81tt; 29.71t.

EXAMPLE 16

(4α, 6β)-4a,5,9,10,11,12-hexahydro-1-bromo-3-methoxy-6H-benzofuro[3a,3,2-ef] [2]benzazepin-6-ol (N-demethyl-bromogalanthamine).
(general formula (I) where: $R_2=Me$, $X_1=Br$, $R_4=X_2=Y_2=H$, $Y_1=OH$) and (4α,6β)-4a,5,9,10,11,12-hexahydro-1-bromo-3-methoxy-6H-benzofuro[3a,3,2-ef] [2]benzazepin-6-ol (N-dimethyl-epibromogalanthamine)
(general formula) (I) where: $R_2=Me$, $X_1=Br$, $R_4=X_2=Y1$ [sic]=H, Y2 [sic]=OH)

3.0 g (11.8 mmol) of $LiAlH(t-B_4O)_3$ in 15 ml of THF are added dropwise to a suspension of 1.0 g (2.6 mmol) of (I) ($R_2=Me$, $R_4=CHO$, $X_1=Br$, $X_2=H$, $Y_1=Y_2=O$) in 5 ml of THF at 0° C. in the course of 30 minutes. After the reaction mixture has been stirred at 0° C. for 30 minutes, it is boiled under reflux. After the mixture has been boiled for 22 hours, the complex formed with the reagent is destroyed with $H_2O$, and 10 ml of 25% strength $NH_4OH$ solution are added to the reaction mixture. After the mixture has been stirred at room temperature for 30 minutes, the solvent is concentrated to half in vacuo, the mixture is transferred into a shaking funnel, 10 ml of 25% strength $NH_4OH$ solution are added and the mixture is extracted with 3×20 ml of $CH_2Cl_2$. The combined organic phases are dried with $Na_2SO_4$ and filtered and the solvent is evaporated off in vacuo. Purification of the residue by chromatography (60 g of $SiO_2$ silica gel $CHCl_3:MeOH=95:5\rightarrow9:1\rightarrow8:2$) gives two products.

300.0 mg (32.2% of N-demethyl-bromogalanthamine (general formula (I) where $R_2=Me$, $X_1=Br$, $R_4=X_2=Y_2=H$, $Y_1=OH$) as a colorless foam and 270 mg (29.0% of N-dimethyl-bromogalanthamine (general formula (I) where $R_2=Me$, $X_1=Br$, $R_4=X_2=Y_1=H$, $Y_2=OH$) as a colorless foam.

Data for N-demethyl-epibromo-galanthamine:

Molecular weight: $C_{16}H_{18}BrNO_3$:352.21

IR(KBr): 781.60w; 834.28w; 976.63w; 1050.28m; 1179.73m; 1211.87m; 1280.07m; 1435.24m; 1486.10m; 1616.37m; 2923.54w: 3700–2900 mbr.

$^1$H—NMR ($CDCl_3$): 6.86 (s, 1H); 5.92 (AB, 2H); 4.56 (m, 2H); 4.50 and 3.82 (AB, 2H); 3.80 (s, 3H); 3.28 (m, 2H); 2.52 (m, 1H); 2.20–1.70 (m, 3H).

$^{13}$C—NMR ($CDCl_3$): 146.73s; 143.91s; 134.10s; 132.17s; 132.17d; 131.48d; 126.34d; 115.34d; 112.44s; 88.51d; 62.81d; 56.10q; 52.34t; 49.25s; 46.82t; 40.52t; 32.07t.

EXAMPLE 17

(4α6β)-4a,5,9,10,11,12-hexahydro-1-bromo-3-methoxy-11-methyl-6H-benzofuro[3a,3,2,-ef] [2]benzazepin-6-ol (N-demethyl-bromogalanthamine)
(general formula (I) where: $R_2=R_4=Me$, $X_1=Br$, $X_2=Y_2=H$, $Y_1=OH$)

Method 1:

5 ml of 89% strength HCOOH and 5 ml of 37% strength $CH_2O$ are added to a solution of 2.0 g (5.6 mmol) of (I) ($R_2=Me$, $X_1=Br$, $R_4=X_2=Y_2=H$, $Y_1=OH$) in 20 ml of $H_2O$) and the mixture is boiled under reflux. After the reaction mixture has been boiled for 15 minutes, it is diluted with $H_2O$, the pH is brought to 9 with 25% strength $NH_4OH$ and the mixture is extracted with 3×20 ml of $CH_2Cl_2$. The combined organic phases are dried with $Na_2SO_4$ and filtered and the solvent is evaporated off in vacuo. Purification of the residue by chromatography 150 g of $SiO_2$ silica gel $CHCl_3:MeOH=97:\rightarrow95:5$) gives a colorless foam.

Yield: 2.0 g (96.4%)

Method 2:

100 ml (100 mmol) of a 1 M solution of L-Selektride are added dropwise to a suspension of 10 g (26.4 mmol) of (I) ($R_2=Me$, $R_4=CHO$, $X_1=Br$, $X_2=H$, $Y_1=Y_2=O$) in 200 ml of THF at 0° C. in the course of 30 minutes. After the mixture has been stirred at 0° C. for 60 minutes the reagent is destroyed with $H_2O$, and 100 ml of 25% strength NH$_4$OH solution are added to the reaction mixture. After the mixture has been stirred at room temperature for 30 minutes, the solvent is concentrated to half in vacuo, the mixture is transferred into a shaking funnel, 100 ml of 25% strength NH$_4$OH are added and the mixture is extracted with 3×200 ml of CH$_2$Cl$_2$. The combined organic phases are dried with Na$_2$SO$_4$ and filtered and the solvent is evaporated off in vacuo. 50 ml of H$_2$O, 30 ml of 98% strength HCOOH and 30 ml of 37% strength CH$_2$O solution are added to the residue and the reaction mixture is boiled under reflux. After the mixture has been boiled for 15 minutes, the reaction is neutralized with NH$_4$OH and the extracted with 3×200 ml of CH$_2$Cl$_2$. The combined organic phases are dried over Na$_2$SO$_4$ and filtered and the solvent is evaporated off in vacuo. Purification of the residue by chromatography (600 g of SiO$_2$ silica gel CHCl$_3$:MeOH=9:1→8:2) gives a colorless foam.

Yield: 6.4 g (66.2%).

EXAMPLE 18
Optical separation of (±)galanthamine

A solution of 672.2 mg (1.74 mmol) of (+)di-p-toluyl-D-tartaric acid in 4 ml of MeOH is added to a solution of 500 mg of (±)galanthamine (1.74 mmol), compound (I) (R$_2$=R$_4$=Me, X$_1$=X$_2$=Y$_2$=H, Y$_1$=OH), in 1.0 ml of MeOH at room temperature. After the mixture has been left to stand in a refrigerator for 24 hours, the crystalline substance which has precipitated out is filtered and washed with MeOH. The mother liquor is saved for the other isomer. Recrystallization from EtOH gives 450 mg of (−)galanthamine (+)di-p-toluoyl-tartrate (compound (II), R$_2$=R$_4$=Me, R$_5$=X$_1$=X$_2$=Y$_2$=H, Y$_1$=OH, Z=(+)di-p-toluoyl-tartrate), melting point: 182 to 184° C. The free base is liberated from the salt with CHCl$_3$/NH$_4$OH. [α]$_D$=−101.8° C.

The methanolic mother liquor is evaporated, the base is liberated with CHCl$_3$/NH$_4$OH and dissolved in 0.5 ml of MeOH, and a solution of 215 mg (0.55 mmol) of (−)di-p-toluyl-L-tartaric acid is added. After the mixture has been left to stand in a refrigerator for 24 hours, the material which has precipitated out is filtered and washed with MeOH. Recrystallization from EtOH gives 242 mg of (+)galanthamine(−)di-p-toluoyl-tartrate (compound (II) R$_2$=R$_4$Me, R$_5$=X$_1$=X$_2$=Y$_2$=H, Y$_1$=OH, Z=(−)di-p-toluoyl-tartrate), melting point: 144 to 148° C. The salt is converted into the free base with CHCl$_3$ [sic]/NH$_4$OH. [α]$_D$=+98.9° C.

EXAMPLE 19
4a,5,9,10,11,12-hexahydro-1-bromo-3-methoxy-11-formyl-6H-benzofuro[3a,3,2-ef] [2]benzazepine 6-ethylene ketal (general formula (I) where R$_2$=Me, R$_4$=CHO, X$_1$=Br, X$_2$=H, Y$_1$, Y$_2$=—O—(CH$_2$)$_2$—O—)

5.0 g of the compound (I) where R$_2$=Me, R$_4$=CHO, X$_1$=Br, X$_2$=H, Y$_1$, Y$_2$=O, 10.0 g ethylene glycol and 0.05 g of p—TsOH were heated to the reflux temperature in 100 ml of toluene (2-phase mixture at room temperature) with vigorous mechanical stirring (homogeneous from about 90° C.) and the mixture was boiled for 2 hours, water being separated off. After cooling, the phases were separated (the toluene phase being the upper phase), the ethylene glycol phase was extracted twice with 20 ml of toluene and the combined toluene phases were shaken with 2×50 ml of saturated NaHCO$_3$ solution, dried over Na$_2$SO$_4$ and evaporated.

Yield: 5.40 g of a yellowish foam (96.7% of theory crude), which crystallized overnight.

Column chromatography of 1.0 g (60 g of silica gel 60, CHCl$_3$/1 to 2% of MeOH) gave: 0.62 g of a colorless foam which crystallized from EtOAc.

Melting point: 212 to 214° C.

Molecular weight: C$_{19}$H$_{20}$BrNO$_5$:422.28

$^1$H—NMR (CDCl$_3$): 812 (d, H), 6.87 (s, H), 6–06 (t, H), 5.72 (d,H), 5.64 (d, H/2), 5.11 (d/H2), 4.54 (b, H), 4.48 (d, H/2), 4.31 (d, H/2), 3.50–4.10 (m, 6H), 3.82 (s, 3H), 2.65 (d, H), 2.27 (d, H), 1.74–2.10 (m, 2H).

$^{13}$C—NMR (CDCl$_3$): 162.40, 161.65, 147.08, 144.81, 144.55, 132.14, 131.96, 127.68, 127.48, 115.68, 115.43, 126.71, 126.44, 113.12, 111.59, 102,04, 87.07, 86.90, 65.14, 64.23, 55.88, 51.43, 46.11, 48.41, 40.67, 39.27, 35.96, 32.94.

EXAMPLE 20
4a,5,9,10,11,12-hexahydro-1-bromo-3-methoxy-11-formyl-6H-benzofuro[3a,3,2-ef] [2]benzazepine 6-propylene ketal (general formula) (I) where R$_2$=Me, R$_4$=CHO, X$_1$=Br, X$_2$=H, Y$_1$,Y$_2$=—O—CH$_2$—CH(CH$_3$)—O—)

100 g of the compound (I) where R$_2$=Me, R$_4$=CHO, X$_1$=Br, X$_2$=H, Y$_1$,Y$_2$=O, 100 g of propylene glycol and 0.5 g of H$_2$SO$_4$ were heated to the reflux temperature in 800 ml of toluene (2-phase mixture at room temperature) with vigorous mechanical stirring (homogeneous from about 90° C.) and the mixture was boiled for 14 hours, water being separated off. After cooling, the phases were separated (the toluene phase being the upper phase), the propylene glycol phase was extracted twice with 100 ml of toluene and the combined toluene phases were shaken with 2×200 ml of saturated NaHCO$_3$ solution, dried over Na$_2$SO$_4$ and evaporated.

Yield: 115.3 g of a yellowish foam (100% of theory crude), which crystallized overnight.

Column chromatography of 1.0 g (60 g of silica gel 60, CHCl$_3$/1 to 2% of MeOH) gave: 0.80 g of a colorless foam which crystallized from EtOAc.

Melting point: 170 to 171° C.

Molecular weight: C$_{20}$H$_{22}$BrNO$_5$:436.28

$^1$H—NMR (CDCl$_3$): 8.12 (d, H), 6.88 (s, H), 5.96–6.17 (m, H), 5.75 (dd, H), 5.68 (d, H/2), 5.10 (d, H/2), 4.53 (b, H), 4,48 (d, H/2), 4.31 (d, H/2),3.12–4.38 (m, 5H), 3.82 (s, 3H), 2.56–2.80 (m, H), 2.05–2.35 (dd, H), 1.83–2.05 (m, 2H), 1.22–1.47 (m, 3H).

$^{13}$C—NMR(CDCl$_3$): 162.48, 161.72, 147.17, 144.89, 144.64, 132.16, 129.04, 128.51, 128.57, 127.82, 127.70, 127.61, 115.70, 115.48, 127.09, 126.77, 126.5, 113.20, 111.66, 102.38, 102.22, 87.25, 87.07, 73.38, 72.46, 71.67, 71.41, 71.23, 70.55, 70.28, 55.92, 51.52, 46.18, 48.43, 40.77, 39.29, 36.07, 35.97, 34.58, 33.68, 33.44, 33.13, 18.68, 17.59, 17.45.

Note NMR$^1$ diastereomers: Because of the chiral center additionally introduced by means of the (+/−)propylene group, diastereomers are formed which result in an additional splitting of the signal in addition to that caused by the formyl group.

EXAMPLE 21
4a,5,9,10,11,12-hexahydro-3-methoxy-11-methyl-6H-benzofuro[3a3,2-ef] [2]benzazepine 6-ethylene ketal (general formula (I) where R$_2$=Me, R$_4$=CH$_3$, X$_1$=X$_2$=H, Y$_1$, Y$_2$=—O—CH$_2$-CH$_2$—O—).

2.0 g of the compound (I) where R$_2$=Me, R$_4$=CHO, X$_1$=Br, X$_2$=H, Y$_1$,Y$_2$=O—(CH$_2$)$_2$—O— were suspended in 50 ml of anhydrous THF, the suspension was cooled to 0° C., 20 ml of LiAlH$_4$(diethyl ether (1M) were added dropwise in the course of 5 minutes and the mixture was warmed to room temperature. It was then stirred at the reflux temperature (45 to 52° C.) for 12 hours and cooled, 3 ml of THF/water (2:1) were added dropwise, and the mixture was rendered alkaline with 50 ml of NH$_4$OH (25%) and extracted 4 times with 50 ml of EtOAc. The organic phases were dried over Na$_2$SO$_4$ and evaporated.

Yield: 1.52 g of a yellowish oil (92.9% of theory).

Column chromatography (80 g of silica gel 60, EtOAc/MeOH 8:2) gave: 0.82 g of colorless crystals Melting point: 109–110° C.

Molecular weight: (C$_{19}$H$_{23}$NO$_4$): 329.40

$^1$H—NMR (CDCl$_3$): 1.65 (ddd, 1H), 2.10 (ddd, 1H), 2.15 (dd, 1H), 2.40 (s, 3H), 2.65 (dd, 1H), 3.05 (ddd, 1H), 3.20 (ddd, 1H), 3.60 (d, 1H), 3.80 (s, 3H), 3.90–4.05 (m, 4H), 4.10 (d, 1H), 4.55 (dd, 1H), 5.65 (d, 1H), 6.15 (d, 1H), 6.55, 6.60 (2x d, 2H)

$^{13}$C—NMR (CDCl$_3$): 33.2 (t), 33.8 (t), 41.7 (q), 47.8 (t), 53.8 (s), 55.5 (q), 60.2 (t), 64.0, 65.0 (2x t), 87.1 (d), 102.5 (s), 110.9 (d), 121.1 (d), 125.9 (d), 128.7 (s), 128.9 (s), 131.8 (d), 143.8 (s), 146.5 (s).

EXAMPLE 22

4a,5,9,10,11,12-hexahydro-3-methoxy-11-methyl-6H-benzofuro[3a,3,2-ef] [2]benzazepine 6-(2-hydroxyethyl) ether (general formula) (I) where R$_2$=Me, R$_4$=CH$_3$, X$_1$=X$_2$=H, Y$_1$= —O—CH$_2$—CH$_2$—OH, Y$_2$=H)

1.0 g of the compound (I) where R$_2$=Me, R$_4$=CHO, X$_1$=Br, X$_2$=H, Y$_1$,Y$_2$=O—(CH$_2$)$_2$—O— were dissolved in 25 ml of THF, the solution was cooled to 0° C., 9 ml of LiAlH$_4$/THF (1M) were added dropwise in the course of 5 minutes and the mixture was stirred at 0° C. for 30 minutes. It was now heated at the reflux temperature for 48 hours and cooled, 25 ml of NH$_4$OH (25% strength) were added dropwise and the mixture was extracted 4 times with 20 ml of EtOAc. The organic phases were dried over Na$_2$SO$_4$ and evaporated:

Yield: 0.76 g of a yellowish oil (92.9% of theory).

Column chromatography (40 g of silica gel 60, CHCl$_3$/2–7% of MeOH) gave: 0.62 g of a colorless foam.

Molecular weight: (C$_{19}$H$_{24}$NO$_4$): 330.40

$^1$H—NMR (CDCl$_3$): 1.52 (dd, H), 1.85 (td, H), 2.10 (dt, H), 2.35 (s, 3H), 2.82 (d, H), 3.02 (d, H), 3.20 (b, H, D$_2$O-exchangeable), 3.24 (d,H), 3.53–3.72 (m, 5H), 3.78 (s, 3H), 3.94 (t, H), 4.10 (d, H), 4.54 (b, H), 5.94 (d, H), 6.22 (d, H), 6.33 (d, H), 6.61 (d, H).

$^{13}$C—NMR (CDCl$_3$): 26.50, 34.35, 41.57, 48.01, 53.57, 55.72, 60.17, 61.78, 68.42, 69.48, 86.85, 111.06, 121.22, 124.60, 128.95, 129.21, 131.86, 143.88, 146.15.

EXAMPLE 23

4a,5,9,10,11,12-hexahydro-1-bromo-3-methoxy-11-demethyl-6H-benzofuro[3a,3,2-ef] [2]benzazepine 6-ethylene ketal (general formula (I) where R$_2$=Me, R$_4$=H, X$_1$=Br, X$_2$=H, Y$_1$,Y$_2$=—O—CH$_2$—CH$_2$—O—)

0.11 g of the compound (I) where R$_2$=Me, R$_4$=CHO, X$_1$=Br, X$_2$=H, Y$_1$,Y$_2$=O—(CH$_2$)$_2$—O— was dissolved in 10 ml of THF, the solution was cooled to 0° C., 0.3 ml of LiAlH$_4$/THF (1M) was added dropwise in the course of 5 minutes and the mixture was stirred at 0° C. for 30 minutes. Excess THF was evaporated off, the residue was taken up in 10 ml of NH$_4$OH (25% strength) and the mixture was extracted 3 times with 10 ml of EtOAc. The organic phases were dried over Na$_2$SO$_4$ and evaporated.

Yield: 0.13 g of an oily crude product.

Column chromatography (5 g of silica gel 60, CHCl$_3$/2–7% of MeOH) gave: 80 mg of a colorless foam (77.9% of theory)

Molecular weight: (C$_{18}$H$_{20}$BrNO$_4$): 394.27

$^1$H—NMR (CDCl$_3$): 6.82 (s, H), 6.16 (d, H), 5.67 (d, H), 4.55 (b, H), 4.48 (d, H), 3.84–4.08 (m, 5H), 3.78 (s, 3H), 3.04–3.37 (m, 2H), 2.62 (bd, H), 2.15 (dd, H), 1.70–1.95 (m, 3H), $^{13}$C—NMR (CDCl$_3$): 146.69, 144.00, 133.07, 131.29, 129.00, 112.16, 126.30, 115.25, 102.37, 87.28, 65.11, 64.17, 55.78, 52.46, 49.02, 40.13, 33.06.

EXAMPLE 24

4a,5,9,10,11,12-hexahydro-1-bromo-3-methoxy-11-benzyl-6H-benzofuro[3a,3,2-ef] [2]benzazepine 6-ethylene ketal (general formula) (I) where R$_2$=Me, R$_4$=—CH$_2$—Ph, X$_1$=Br, X$_2$H, Y$_1$,Y$_2$=—O—CH$_2$—CH$_2$—O—)

250 mg (0.63 mmol) of the compound (I) where R$_2$=Me, R$_4$=H, X$_1$=Br, X$_2$=H, Y$_1$,Y$_2$=O—(CH$_2$)$_2$—O— (N-demethyl bromonarwedine ethylene ketal) and 63 mg (0.63 mmol) of triethylamine were initially introduced into 15 ml of absolute tetrahydrofuran, 108 ml (0.63 mmol) of benzyl bromide were added at room temperature and the mixture was then stirred for 24 hours. 50 ml of water were added to the reaction mixture and the aqueous phase was extracted 3 times with 20 ml of ethyl acetate each time. The combined organic phases were washed once with saturated aqueous sodium chloride solution, dried (over Na$_2$HO$_4$ [sic]) and evaporated.

Yield: 260 mg (84.7% of theory) of colorless crystals.

Melting point: 118–119° C.

TLC: EtOAc: MeOH=9:1

Molecular weight: (C$_{25}$H$_{26}$BrNO$_4$): 484.39

$^1$H-NMR (CDCl$_3$; d (ppm)): 1.65 (ddd, 1H), 2.05–2.30 (m, 2H), 2.65 (dd, 1H), 3.00–3.30 (m, 2H), 3.70 (s, 2H), 3.80 (s, 3H), 3.90–4.20 (m, 5H), 4.35 (dd, 1H), 4.60 (ddd, 1H), 5.70 (d, 1H), 6.25 (d, 1H), 6.85 (s, 1H), 7.25–7.30 (m, 5H).

$^{13}$C-NMR (CDCl$_3$, d (ppm)): 33.1 (d), 33.4 (t), 48.5 (s), 50.7 (t), 55.8 (q), 56.4 (t), 56.9 (t), 64.2, 65.1 (2*t), 87.4 (d), 102.3 (s), 113.6 (s), 115.6 (d), 126.6, 128.2, 128.9 (3*d), 127.1 (d), 3.1 (s), 137.9 (s), 144.2 (s), 146.3 (s).

EXAMPLE 25

4a,5,9,10,11,12-hexahydro-1-bromo-3-methoxy-11-demethyl-6H-benzofuro[3a,3,2-ef] [2]benzazepin-6-one (general formual (I) where R$_2$=Me, R$_4$=H, X$_1$=Br, X$_2$=H, Y$_1$,Y$_2$=O)=N-demethylbromonarwedine 250 mg (0.63 mmol) of the compound (I) where R$_2$=Me, R$_4$=H, X$_1$=Br, X$_2$=H, Y$_1$,Y$_2$=O-(CH$_2$)$_2$-O(=N-demethylbromonarwedine ethylene ketal) were dissolved in 20 ml of 2N hydrochloric acid and the solution was heated at 100° C. for 15 minutes. 20 ml of concentrated aqueous ammonia were then added, the reaction mixture was heated briefly and cooled, and a precipitate was obtained, which was filtered off with suction and dried at 50° C.(20 mm.

Yield: 130 mg (58.6% of theory) of colorless crystals

Melting point: 173–174° C.

TLC: EtOAc: MeOH=8:2

Molecular weight: (C$_{16}$H$_{16}$Br, NO$_3$), 350.21

$^1$H-NMR (DMSO-d6, d (ppm)): 1m90–2.15 (m, 2H), 2.75 (dd, 1H), 2.95 (dd, 1H), 3.10–3.35 (m, 2H), 3.75 (s, 3H), 3.90 (d, 1H), 4.40 (d, 1H), 4.55 (dd, 1H), 5.90 (d, 1H), 6.90 (s, 1H), 7.05 (d, 1H)

$^{13}$C-NMR (DMSO-d6, d (ppm)): 36.3 (d), 37.0 (t), 45.6 (s), 49.5 (t), 51.3 (t), 55.9 (g), 87.6 (d), 112.5 (s), 116.0 (d), 126.6 (d), 129.6 (s), 132.0 (s), 143.7 (s), 144.8 (d), 146.6 (s), 194.0 (s)

EXAMPLE 26

4a,5,9,10,11,12-hexahydro-3-methoxy-11-demethyl-6H-benzofuro[3a,3,2-ef] [2]benzazepin-6-one (general formula (I) where R$_2$=Me, R$_4$=H, X$_1$=X$_2$=H, Y$_1$,Y$_2$=O)

EXAMPLE 27

4a,5,9,10,11,12-hexahydro-3-methoxy-11-benzyl-6H-benzofuro[3a,3,2-ef] [2]benzazepin-6-one (general formula (I) where R$_2$=Me, R$_4$=CH$_2$-Ph, X$_1$,X$_2$=H, Y$_1$,Y$_2$=O)

EXAMPLE 28

4a,5,9,10,11,12-hexahydro-3-methoxy-11-methyl-6H-benzofuro[3a,3,2-ef] [2]benzazepine 6-propylene ketal (general formula (I) where $R_2$=Me, $R_4$=CH$_3$, $X_1$=$X_2$=H, $Y_1,Y_2$=O—CH$_2$-CH(CH$_3$)-O-)

37.5 g of LiAlH$_4$ were introduced into a predried 4 l multi-necked flask under argon, and 800 ml of THF were allowed to run in from a dropping funnel, the temperature rising to about 45° C. with vigorous foaming (depends on the water content of the THF and of the reaction flask). A suspension of 114 g of the compound (I) where $R_2$=Me, $R_4$=CHO, $X_1$=bromine, $X_2$=H, $Y_1,Y_2$=O—CH$_2$-CH(CH$_3$)-O— (crude) in 400 ml of THF was now added dropwise in the course of 15 minutes, the temperature rising to the reflux temperature (about 65–68° C.). The mixture was now heated at the reflux temperature for 10 hours, with mechanical stirring, and cooled and 100 ml of water in 100 ml of THF were added dropwise, while cooling.

Removal of 10 ml, rendering alkaline with NH$_4$OH and extraction with EtOAc (3×20 ml) gave, after evaporation, an oily product.

Column chromatography (5 g of silica gel 60, CHCl$_3$/3–5% of MeOH) of 0.17 g gave: 0.1 g of a colorless foam Molecular weight: (C$_{20}$H$_{25}$NO$_4$): 343.42

$^1$H-NMR (CDCl$_3$): 6.60 (dd, 2H), 6.16 (dt, H), 5.68 (dd, H), 4.55 (m, H), 4.38–4.00 (m, 3H), 3.80 (s, 3H), 3.68–2.95 (m, 4H), 2.78–2.80 (m, H), 2.35 (s, 3H), 2.24–2.02 (m, 2H), 1.62 (bd, H), 1.28 (t, 3H)

$^{13}$C-NMR (CDCl$_3$): 146.59, 143.92, 132.04, 131.90, 129.57, 129.16, 128.86, 128.76, 128.39, 127.44, 126.92, 126.12, 126.02, 121.16, 111.05, 110.90, 110.77, 102.87, 102.73, 87.23, 73.15, 72.24, 71.43, 71.12, 70.44, 70.17, 60.28, 55.59, 55.53, 55.45, 53.83, 47.87, 47.80, 47.75, 41.80, 41.70, 34.84, 33.95, 33.66, 33.37, 18.66, 17.62, 17.43

Note NMR, diastereomers: Because of the chiral center additionally introduced by means of the (+/−) propylene group, diastereomers are formed which have the effect of a splitting of the signal in addition to that caused by the formyl group.

EXAMPLE 29

4a,5,9,10,11,12-hexahydro-3-methoxy-11-methyl-6H-benzofuro[3a,3,2-ef] [2]benzazepin-6-one, narwedine. (General formula (I) where $R_2$=Me, $R_4$=CH$_3$, $X_1$=$X_2$=H, $Y_1,Y_2$=O)

37.5 g of LiAlH$_4$ were introduced into a predried 4 l multi-necked flask under argon, and 800 ml of THF were allowed to run in from a dropping funnel, the temperature rising to about 45° C. with vigorous foaming (depends on the water content of the THF and of the reaction flask). A suspension of 114 g of the compound (I) where $R_2$=Me, $R_4$=CHO, $X_1$=bromine, $X_2$=H, $Y_1,Y_2$=O—CH$_2$-CH(CH$_3$)-O— (crude) in 400 ml of THF was now added dropwise in the course of 15 minutes, the temperature rising to the reflux temperature (about 65–68° C.). The mixture was then heated at the reflux temperature for 10 hours, with mechanical stirring, and cooled, and 100 ml of water in 100 ml of THF were added dropwise, while cooling.

The pH was then brought to 0 to 1 with 1.25 liters of 2N HCl and 60 ml of concentrated HCl and the mixture was stirred at 60° C. for 30 minutes, subsequently transferred into a 5 liter separating funnel, covered with a layer of 1 liter of EtOAc, brought to pH 10 with NH$_4$OH (about 250 ml) and extracted. The aqueous phase was extracted once more with 1 l of EtOAc+300 ml of THF, the precipitate was then filtered off over Celite and extraction was carried out a further two times with 500 ml of EtOAc. The combined organic phases were dried over Na$_2$SO$_4$ and evaporated.

Yield: 64.8 g (86.9% of theory crude) of yellow crystals
Molecular weight: 285.32 (C$_{17}$H$_{19}$NO$_3$)
TLC: CHCl$_3$/MeOH (5%)
Melting point: 189–192° C.

EXAMPLE 30

(−)narwedine:

122.4 g of (+/−)narwedine were heated at the reflux temperature in 1.9 l of EtOH (96% strength)/triethylamine (9:1) until a homogeneous solution formed. The mixture was then cooled slowly, 4.0 g of (−)narwedine were added at 68° C. and the mixture was stirred at 40° C. for 7 days. Cooling to room temperature, filtration with suction and drying of the crystalline precipitate gave (−)narwedine (fraction I). The mother liquor was evaporated to dryness, the residue was heated to the reflux temperature with 200 ml of ethanol (95% strength)/triethylamine (9:1), and 0.4 g of (−)narwedine was added and the mixture stirred at 40° C. for 7 days in the manner described above. Cooling, filtration with suction and drying gave (−)narwedine (fraction II).

Yield:
Fraction I: 98.6 g of colorless crystals (80.5% of theory)
Fraction II: 7.4 g (6.0% of theory)
Optical rotation: Fraction I: $[\alpha]^{18}$=−407° (c=1.5/CHCl$_3$)
Fraction II: $[\alpha]^{18}$=−401° (c=1.5/CHCl$_3$)
Molecular weight: C$_{17}$H$_{19}$NO$_3$ (285.32)
Melting point: 189–192° C.

EXAMPLE 31

(−)galanthamine 98.6 g of (−)narwedine were added in portions to 1 l of L-Selektride in THF (1 molar) at room temperature and the mixture was stirred for 1 hour. 100 ml of MeOH were then slowly added dropwise, the cloudy solution was evaporated to dryness and the residue was taken up in 3 l of ethanol (96%). The mixture was acidified to pH 1 dropwise with a solution of aqueous 60% strength HBR in EtOH (1:1) and was left to stand overnight at 0° C. The crystals which had precipitated out were filtered off with suction and dried.

Yield: 120.1 g (94.5% of theory)
Optical rotation: $[\alpha]^{18}$=−88° (c=1.5/H$_2$O)
Molecular weight: C$_{17}$H$_{21}$NO$_3$×HBr (368.25)
Melting point: 244–247° C. (decomposition)

EXAMPLE 32

3-Benzoyloxy-N-4-(benzyloxyphenethyl)-6-bromo-4-methoxy-N-methylbenzamide (general formula (Va) with $R_1$, $R_3$=benzyl, $R_2$=$R_4$=CH$_3$, $X_1$=Br, $X_2$=H, $Z_1$=O, $Z_2$=H$_2$).

20.0 g of 3-benyloxy-6-bromo-4-methoxybenzoic [sic] acid were dissolved in 250 ml of chloroform p.a. and then 21.6 ml of thionyl chloride (35.29 mg=0.297 mol=5 eq.) were added and the mixture was refluxed for 3 hours, and then excess CHCl$_3$+SOCl$_2$ were distilled off. The resulting acid chloride was taken up in 150 ml of CHCl$_3$.

14.24 g of O-benzyl-N-methyltyramine were dissolved in 60 ml of CHCl$_3$ p.a. and then 100 ml of 2N NaOH were added. The dissolved acid chloride was added to the 2-phase mixture at room temperature with vigorous stirring and the mixture was stirred overnight. The phases were then separated. The organic phase was washed with H$_2$O, dried over Na$_2$SO$_4$ and concentrated by evaporation. The oil obtained was recrystallized from 250 ml of ethanol.

Yield: 27.76 g, 83% of theory, of colorless crystals.
TLC: petroleum ether/EtOAc (25:75)
$^1$H-NMR (CDCl$_3$): because of the amide there are two conformers (rotamers). 2.69+3.12 (2s, each 1.5H); 2.95+3.21 (2t, each 1H); 3.75 (t, 1H); 3.9 (s, 3H) 4.96–5.14 (m, 4H), 7.1–7.48 (m, 16H).

$^{13}$C-NMR (CDCl$_3$): 32.26, 36.55, 32.48, 33.39, 48.75, 52.34, 56.14, 70.92, 71.10, 112.82, 113.05, 114.77, 115.69, 127.23, 128.47, 129.73, 129.78.

EXAMPLE 33
6-Bromo-3-hydroxy-N-(4-hydroxyphenethyl)-4-methoxy-N-methylbenzamide (general formula (Va) with R$_1$=R$_3$=H, R$_2$=R$_4$=CH$_3$, X$_1$=Br, X$_2$=H, Z$_1$=O, Z$_2$=H$_2$).

5.0 g of 3-benzyloxy-N-4-(benzyloxyphenethyl)-6-bromo-4-methoxy-N-methylbenzamide (general formula (Va) with R$_1$,R$_3$=benzyl, R$_2$=R$_4$=CH$_3$, X$_1$=Br, X$_2$=H$_1$, Z$_1$=O, Z$_2$=H$_2$) were heated with 50 ml of ethanol and 21.6 ml of HBr to 60° C. and the heated mixture was stirred for 9 hours. The solution was slowly poured into 1 l of ice-water and was stirred for two hours to allow the product to crystallize. The precipitate was filtered off with suction, washed with water and dried.

Yield: 3.23 g (95.22% of theory) of colorless crystals.
TLC: CHCl$_3$:MeOH=9:1
Melting point: 162–166.5° C.
$^1$H-NMR (CDCl$_3$/DMSO): because of the amide there are two isomers. 2.49+2.81 (2s, each 1.5H); 3.08+3.42 (2t, each 1H), 3.65 (s, 3H); 6.43–6.6 (m, 4H); 6.72 (s, 1H); 6.88 (s, 1H), 8.31–8.59 (b, 2H).
$^{13}$C-NMR (CDCl$_3$/DMSO): 32.08+33.52, 32.36+36.54, 48.91+54.49, 55.92, 113.97, 114.39, 115.43+115.28, 129.44+129.30, 168.61+168.97.

EXAMPLE 34
4a,5,9,10,11,12-Hexahydro-1-bromo-3-methoxy-11-methyl-12-oxo-6H-benzofuro[3a,3,2-ef] [2]benzazepin-6-one (general formula (Ia) with R$_2$=R$_4$=CH$_3$, X$_1$=Br, X$_2$=H, Y$_1$,Y$_2$=O, Z$_1$=O, Z$_2$=H$_2$).

40.5 g of potassium hexacyanoferrate(III) (123 mol) and 18 g of K$_2$CO$_3$ (0.13 mol) were dissolved in 2.7 l of toluene and 180 ml of water and the solution was heated to 60° C. Then 9.0 g of 6-bromo-3-hydroxy-N-(4-hydroxyphenethyl)-4-methoxy-N-methylbenzamide (general formula (Va) with R$_1$,R$_3$=H, R$_2$=R$_4$=CH$_3$, X$_1$=Br, X$_2$=H, Z$_1$=O, Z$_2$=H$_2$) (0.024 mol) were added. The reaction mixture was subjected to vigorous mechanical stirring for 35 minutes. The resulting polymer [lacuna] filtered over Celite. The aqueous phases were separated off, and the toluene phase was washed with saturated NaCl, dried over Na$_2$SO$_4$ and concentrated by evaporation.

Crude yield: 5.39 g (60.22% of theory) of a yellowish oil.
1.8 g were chromatographed over 100 g of silica gel (eluent: CHCl$_3$:MeOH=98:2).
Yield: 1.13 g (37.8% of theory) of colorless crystals.
TLC: CHCl$_3$:MeOH=95:5
Melting point: 218–222° C.
$^1$H-NMR (CDCl$_3$): 1.92+2.48 (dd, 2H); 2.75+3.1 (dd, 2H); 3.34+3.82 (dd, 2H); 3.91 (s, 3H); 4.83 (t, 1H); 5.9–6.0+6.3–6.39 (dd, 2H), 7.11 (s, 1H).
$^{13}$C-NMR (CDCl$_3$/DMSO): 34.00, 36.44+36.58, 48.44, 48.55, 56.31, 89.15, 113.88, 118.55, 122.84, 125.84, 129.35, 145.60, 146.02, 146.61, 164.57, 192.93

EXAMPLE 35
4a,5,9,10,11,12-hexahydro-1-bromo-3-methoxy-11-methyl-12-oxo-6H-benzofuro[3a,3,2-ef] [2]benzazepine-6,6-propylene glycol ketal (general formula (Ia) with R$_2$=R$_4$=CH$_3$, X$_1$=Br, X$_2$=H, Y$_1$,Y$_2$=O—CH$_2$CH(CH$_3$)O—, Z$_1$=O, Z$_2$=H$_2$).

1 g of precursor (12) (0.0026 mol), 50 ml of toluene, 2 ml of propylene glycol and 0.1 g of p-toluene-sulfonic acid were refluxed on a water separator for 4 hours. After cooling, the solution was extracted with NaHCO$_3$ and H$_2$O, and the extracts were dried over Na$_2$SO$_4$ and concentrated on a rotary evaporator.

Yield: 0.92 g, 79.75% of theory.
0.9 g of product were chromatographed over 50 g of silica gel. Eluent CH$_2$Cl$_2$:MeOH=99:1
Fraction 1: 0.34 g of colorless foam (30.1% of theory)
Fraction 2: 0.19 g of colorless foam
Fraction 3: 0.17 g of colorless foam
TLC: CHCl$_3$:MeOH=95:5
Fraction 1:
$^1$H-NMR (CDCl$_3$): 6.95 (s, 1H), 5.38–5.60 (m, 2H), 4.64 (m, 1H), 4.15 (m, 1H), 3.80 (s, 3H), 3.35–4.10 (m, 2H), 3.10 (s, 3H), 3.00 (dd, H), 2.85 (dd, H), 2.15–2.35 (m, 2H), 1.70–1.95 (m, 2H), 1.12–1.25 (m, 3H).
Fraction 2:
$^1$H-NMR (CDCl$_3$): 0.96–1.1 (m, 3H), 1.18–1.32 (m, 3H), 1.40–1.71 (m, 2H), 1.85 (b, H), 1.90–2.20 (m, 2H), 2.35–2.66 (m, 2H), 2.70–2.82 (m, H), 3.10 (s, 3H), 3.20 (b, H), 3.42–3.81 (m, 6H), 3.85 (s, 3H), 4.02 (m, H), 4.20 (m, H), 4.50 (bd, H), 7.05 (s, H).
Fraction 3:
$^1$H-NMR (CDCl$_3$): 0.95–1.1 (m, 3H), 1.20–1.35 (m, 3H), 1.51–1.72 (m, H), 1.82 (b, H), 1.80–2.12 (m, 3H), 2.30–2.68 (m, 2H), 3.12 (s, 3H), 3.20–3.75 (m, 7H), 3.83 (s, 3H), 3.96–4.15 (m, H), 4.22 (m, H), 4.52 (bd, H), 7.07 (s, H).

EXAMPLE 36
Narwedine (general formula (Ia) with R$_2$=R$_4$=CH$_3$, X$_1$=X$_2$=H, Y$_1$,Y$_2$=O, Z$_1$=Z$_2$=H$_2$)

0.35 g of 4a,5,9,10,11,12-hexahydro-1-bromo-3-methoxy-11-methyl-12-oxo-6H-benzofuro-[3a,3,2-ef][2]benzazepine-6,6-propylene glycol ketal (general formula (Ia) with R$_2$=R$_4$=CH$_3$, X$_1$=Br, X$_2$=H, Y$_1$,Y$_2$=O—CH$_2$CH(CH$_3$)O—, Z$_1$=O, Z$_2$=H$_2$) were added with cooling to a solution of 0.2 g of LiAlH$_4$ in 20 ml of anhydrous THF and the mixture was stirred at room temperature overnight. Then 20 ml of 2N HCl were added and the mixture was stirred at 40° C. for 30 minutes, rendered alkaline with concentrated NH$_4$OH and subjected to extraction with ethyl acetate (4×30 ml). Drying over Na$_2$SO$_4$ and concentration of the organic phase by evaporation gave 0.21 g of yellowish oil which was chromatographed over 15 g of silica gel with CHCl$_3$/MeOH (98:2): 0.14 g (61.2% of theory) of narwedine as colorless crystals.
TLC: CHCl$_3$/MeOH (95:5)

EXAMPLE 37
Reduction of compound (12) with L-Selektride to a compound of the general formula (Ia) with R$_2$=R$_4$=CH$_3$, X$_1$=Br, X$_2$=H, Y$_1$=OH, Y$_2$=H, Z$_1$=O, Z$_2$=H$_2$.

1 g of precursor (12) (0.0026 mol) was dissolved in 50 ml of anhydrous THF, and then 7.93 ml of L-Selektride (0.0079 mol=3 eq.) were added and the mixture was stirred at room temperature for three hours. The solution was acidified with 10 ml of 2N HCl, neutralized with 5 ml of NH$_4$OH and subjected to extraction 3 times with ethyl acetate, and the extracts were dried over Na$_2$SO$_4$ and concentrated on a rotary evaporator. Yield: 1.07 g, 106.47% of theory.

The product was chromatographed with 50 g of silica gel, CHCl$_3$:MeOH=98:2

Yield Fr. 34–49:0.31 g

TLC: $CHCl_3$:MeOH=95:5

Melting point: 75.2–80° C.

$^1$H-NMR ($CDCl_3$): 1.65–1.80 (m, H), 1.95–2.17 (m, H), 2.19–2.38 (dt, H), 2.65 (dm, H), 3.13–3.22 (m, H), 3.15 (s, 3H), 3.70–3.88 (m, H), 3.85 (s, 3H), 4.12 (m, H), 4.70 (b,H), 5.50 (d, H), 5.88 (dd, H), 7.08 (s, H).

$^{13}$C-NMR ($CDCl_3$): 29.64, 33.91, 38.01, 48.13, 48.63, 56.12, 60.59, 89.68, 113.47, 117.78, 123.08, 126.20, 130.64, 131.90, 144.61, 146.02, 164.94.

Explanation of the abbreviations used in the

DiBAl-H: Diisobutylaluminum hydride
Red-Al$^R$: Sodium bis-(2-methoxy-ethoxy)-aluminum dihydride
Superhydride$^R$: Lithium trietylborohydride
9-BBN: 9-borabicyclo(3.3.1)nonane
L-Selektride$^R$: Lithium tri-sec-butylborohydride (Aldrich)
K-Selektride$^R$: Potassium tri-sec-butylborohydride (Aldrich)
LS-Selektride$^R$: Lithium trisiamylborohydride (Aldrich)
KS-Selektride$^R$: Potassium trisiamylborohydride (Aldrich)
Aliquat$^R$: 3-methyl-trioctylammonium chloride
SV: Solvent
ML: Mother liquor
THF: Tetrahydrofuran
DMF: Dimethylformamide
EtOAc: Ethyl acetate
TsOH: p-Toluenesulfonic acid
RT: Room temperature Literature

[1] D. H. R. Barton, G. W. Kirby, Proc. Chem. Soc. 392, 1960.
[2] D. H. R. Barton, G. W. Kirby, J. Chem. Soc. 806, 1962.
[3] T. Kametani, T. Yamaki, H. Yagi, K. Fukumoto, J. Chem. Soc. 2602, 1969.
[4] T. Kametani, T. Yamaki, H. Yagi, K. Fukumoto, J. Chem. Soc. Chem. Comm. 25, 1969.
[5] T. Kametani, C. Seino, K. Yamaki, S. Shibuya, K. Fukumoto, K. Kigassawa, F. Satoh, M. Hiiragi, T. Hayasaka, J. Chem. Soc. (C), 1043, 1971.
[6] T. Kametani, K. Yamaki, T. Terui, J. Het. Chem. 10, 35, 1973.
[7] T. Kametani, K. Shishido. E. Hayashi, C. Seino, T. Kohno, S. Shibuya, K. Fukumoto, J. Org. Chem. 36, 1295, 1971.
[8] J. Szewczyk, A. H. Lewin, F. I. Carroll, J. Het. Chem. 25, 1809, 1988.
[9] Edinen Zentar po Chimia Sophia, DE 2945 161 800604, CA. 94, 15945b.
[10] Edinen Zentar po Chimia Sophia, U.S. Pat. No. 4,290, 862 810,922, CA. 95, 212006t.
[11] R. Vlahov, D. Krikorian, V. Tarpanov, G. Spassov, G. Snatzke, H. Duddeck, H. J. Schäfer, K. Kieslich, Izv. Khim. 20, 59, 1987, CA. 108, 150799e.
[12] D. Krikorian, R. Vlahov, S. Parushev, M. Chinova, I. Vlahov, H. Schäfer, H. Duddeck, G. Schnatzke, Tetrahedron Lett. 25, 2969, 1984.
[13] R. Vlahov, D. Krikorian, G. Spassov, M. Chinova, I. Vlahov. S. Parushev, G. Snatzke, L. Ernst, K. Kieslich, W. Abraham, W. Sheldrick, Tetrahedron 45, 3329, 1989.
[14] K. Shimizu, K. Tomioka, S. Yamada, K. Koga, Heterocycles 8, 277, 1977.
[15] K. Shimizu, K. Tomioka, S. Yamada, K. Koga, Chem. Pharm. Bull. 26, 3765, 1978.
[16] J. P. Yardley, H. Fletcher, Synth. 244, 1976.
[17] R. L. Edwards, D. V. Wilson, J. Chem. Soc. 5003, 1961.
[18] S. D. Saraf, Synth. Commun. 13, 7, 1983.
[19] B. Davis, M. Joullie, WO 8808708 A1.
[20] T. Kametani, M. Premila, K. Fukumotu, Heterocycles 4(6), 1111–14, 1976.
[21] Synform 283–93, 1983.
[22] T. Kametani, K. Yamaki, H. Yagi, K. Fukumoto, J. Chem. Soc. C 2601–5, 1969
[23] R. A. Holton, M. P. Sibi, W. S. Murphy, J.Am.Chem.Soc. 110, 314 (1988)
[24] W. C. Shieh, J. A. Carlson, J. Org. Chem. 59, 5463–5465 (1994)
[25] A. B. Smith, S. J. Branca, M. A. Guaciaro, P. M. Wovkulich, A. Korn, Organic Synthesis Coll. Volume 7, 271.
[26] A. Hagedorn, D. Farnum, J. Org. Chem. 42, 3765 (1977).

What is claimed is:

1. A compound of the formula VI:

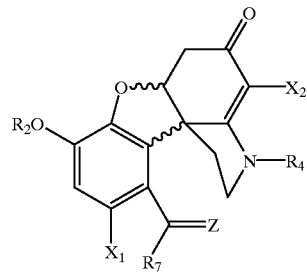

wherein $R_2$, $R_4$, $X_1$ and $X_2$ are either identical or different and are hydrogen, fluorine, chlorine, bromine, iodine, a hydroxyl or alkoxy group, a lower, optionally branched alkyl group which is optionally substituted by at least one halogen, a lower, optionally branched alkenyl group, a lower, optionally branched alkynyl group, an aryl, aralkyl or araloxyalkyl group, the alkyl chain of which is optionally branched and the aromatic nucleus of which is optionally substituted, formyl or unbranched or branched alkylcarbonyl, arylcarbonyl, aralkylcarbonyl, alkyloxycarbonyl, aryloxycarbonyl, aralkyloxycarbonyl, alkylsulfonyl, aralkylsulfonyl or arylsulfonyl which are unsubstituted or substituted by one or more halogens, Z is O, and R₇ is selected from the group consisting of -OR₆, -SR₆, -OR₆OH, and -SR₆SH where R₆ is alkyl, alkenyl, aryl, aralkyl, alkylcarbonyl, arylcarbonyl or aralkylcarbonyl, optionally substituted with at least one halogen.
2. A compound selected from the group consisting of:
(a)
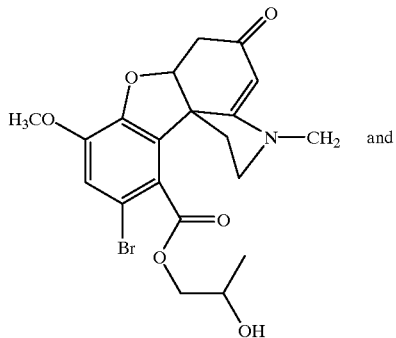
and
(b)
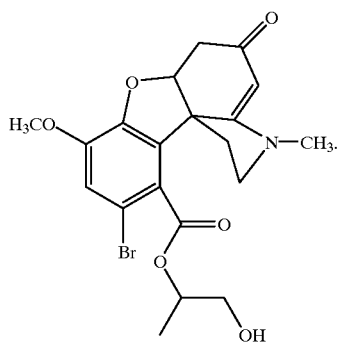
* * * * *

UNITED STATES PATENT AND TRADEMARK OFFICE
CERTIFICATE OF CORRECTION

PATENT NO.   : 6,369,238 B1
DATED        : April 9, 2002
INVENTOR(S)  : Laszlo Czollner et al.

It is certified that error appears in the above-identified patent and that said Letters Patent is hereby corrected as shown below:

<u>Title page,</u>
Item [73], Assignee: "Sanochemia Pharmazeutica, Baltemanngasse (AT)" should read
-- Sanochemia Pharmazeutika AG, Wein, Austria --.

Signed and Sealed this

Eighth Day of October, 2002

*Attest:*

*Attesting Officer*

JAMES E. ROGAN
*Director of the United States Patent and Trademark Office*